(12) United States Patent
Marnfeldt et al.

(10) Patent No.: US 10,994,143 B2
(45) Date of Patent: May 4, 2021

(54) STIMULATION WAVEFORMS WITH HIGH- AND LOW-FREQUENCY ASPECTS IN AN IMPLANTABLE STIMULATOR DEVICE

(71) Applicant: Boston Scientific Neuromodulation Corporation, Valencia, CA (US)

(72) Inventors: Goran N. Marnfeldt, Valencia, CA (US); Kiran K. Gururaj, Valencia, CA (US); Rafael Carbunaru, Valley Village, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 126 days.

(21) Appl. No.: 16/393,606

(22) Filed: Apr. 24, 2019

(65) Prior Publication Data

US 2019/0344083 A1  Nov. 14, 2019

Related U.S. Application Data

(60) Provisional application No. 62/670,551, filed on May 11, 2018.

(51) Int. Cl.
| | | |
|---|---|---|
| *A61N 1/36* | (2006.01) | |
| *A61N 1/372* | (2006.01) | |
| *A61N 1/375* | (2006.01) | |

(52) U.S. Cl.
CPC ..... *A61N 1/36178* (2013.01); *A61N 1/36014* (2013.01); *A61N 1/36125* (2013.01);
(Continued)

(58) Field of Classification Search
CPC ............ A61N 1/36014; A61N 1/36062; A61N 1/36125; A61N 1/36157; A61N 1/36171;
(Continued)

(56) References Cited

U.S. PATENT DOCUMENTS

| | | |
|---|---|---|
| 4,520,825 A | 6/1985 | Thompson et al. |
| 6,181,969 B1 | 1/2001 | Gord |

(Continued)

FOREIGN PATENT DOCUMENTS

| | | |
|---|---|---|
| EP | 2508224 A1 | 10/2012 |
| WO | 2017/106539 | 6/2017 |

OTHER PUBLICATIONS

International Search Report and Written Opinion regarding corresponding PCT Application No. PCT/US2019/028954, dated Aug. 9, 2019.

(Continued)

*Primary Examiner* — George Manuel
(74) *Attorney, Agent, or Firm* — Lewis & Reese, PLLC

(57) ABSTRACT

Waveforms for a stimulator device, and methods and circuitry for generating them, are disclosed having high- and low-frequency aspects. The waveforms comprise a sequence of pulses issued at a low frequency which each pulse comprising first and second charge-balanced phases. One or both of the phases comprises a plurality a monophasic sub-phase pulses issued at a high frequency in which the sub-phase pulses are separated by gaps. The current during the gaps in a phase can be zero, or can comprise a non-zero current of the same polarity as the sub-phase pulses issued during that phase. The disclosed waveforms provide benefits of high frequency stimulation such as the promotion of paresthesia free, sub-threshold stimulation, but without drawbacks inherent in using high-frequency biphasic pulses.

17 Claims, 12 Drawing Sheets

(52) U.S. Cl.
CPC ..... *A61N 1/36157* (2013.01); *A61N 1/36175* (2013.01); *A61N 1/3756* (2013.01); *A61N 1/37229* (2013.01)

(58) Field of Classification Search
CPC ............ A61N 1/36175; A61N 1/36178; A61N 1/37229; A61N 1/3756
See application file for complete search history.

(56) References Cited

U.S. PATENT DOCUMENTS

| | | |
|---|---|---|
| 6,246,912 B1 | 6/2001 | Sluijter et al. |
| 6,516,227 B1 | 2/2003 | Meadows et al. |
| 6,560,490 B2 | 5/2003 | Grill et al. |
| 7,734,340 B2 | 6/2010 | De Ridder |
| 7,890,182 B2 | 2/2011 | Parramon et al. |
| 8,224,453 B2 | 7/2012 | De Ridder |
| 8,364,273 B2 | 1/2013 | De Ridder |
| 8,401,655 B2 | 3/2013 | De Ridder |
| 8,606,362 B2 | 12/2013 | He et al. |
| 8,620,436 B2 | 12/2013 | Parramon et al. |
| 8,712,534 B2 | 4/2014 | Wei |
| 8,774,927 B2 | 7/2014 | DeRidder |
| 8,897,870 B2 | 11/2014 | De Ridder |
| 8,934,981 B2 | 1/2015 | De Ridder |
| 9,259,574 B2 | 2/2016 | Aghassian et al. |
| 9,358,391 B2 | 6/2016 | Zhu et al. |
| 9,462,398 B2 | 10/2016 | DeRidder |
| 9,511,227 B2 | 12/2016 | Biele et al. |
| 9,511,232 B2 | 12/2016 | Biele et al. |
| 9,526,899 B2 | 12/2016 | Biele et al. |
| 9,550,062 B2 | 1/2017 | Khalil et al. |
| 9,656,077 B2 | 5/2017 | De Ridder |
| 9,656,081 B2 | 5/2017 | Feldman et al. |
| 9,737,718 B2 | 8/2017 | Biele et al. |
| 2006/0015153 A1 | 1/2006 | Gliner et al. |
| 2006/0173493 A1 | 8/2006 | Armstrong et al. |
| 2008/0319497 A1 | 12/2008 | Griffith et al. |
| 2012/0092031 A1 | 4/2012 | Shi et al. |
| 2012/0095519 A1 | 4/2012 | Parramon et al. |
| 2012/0095529 A1 | 4/2012 | Parramon et al. |
| 2012/0172946 A1 | 7/2012 | Alataris et al. |
| 2013/0289665 A1 | 10/2013 | Marnfeldt et al. |
| 2015/0080982 A1 | 3/2015 | Funderburk |
| 2015/0157861 A1 | 6/2015 | Aghassian |
| 2015/0231402 A1 | 8/2015 | Aghassian |
| 2015/0360038 A1 | 12/2015 | Zottola et al. |
| 2016/0136427 A1 | 5/2016 | De Ridder |
| 2016/0144183 A1* | 5/2016 | Marnfeldt .......... A61N 1/36142 607/63 |
| 2016/0206883 A1 | 7/2016 | Bornzin et al. |
| 2016/0220820 A1 | 8/2016 | Zottola |
| 2018/0071513 A1 | 3/2018 | Weiss et al. |
| 2018/0071516 A1* | 3/2018 | Weiss .................. A61N 1/0551 |
| 2018/0071520 A1 | 3/2018 | Weerakoon et al. |
| 2018/0071527 A1 | 3/2018 | Feldman et al. |
| 2018/0117332 A1 | 5/2018 | Robinson et al. |
| 2018/0140831 A1 | 5/2018 | Feldman et al. |
| 2019/0083796 A1 | 3/2019 | Weerakoon et al. |

OTHER PUBLICATIONS

U.S. Appl. No. 62/599,546, filed Dec. 15, 2017, Zhang et al.

* cited by examiner

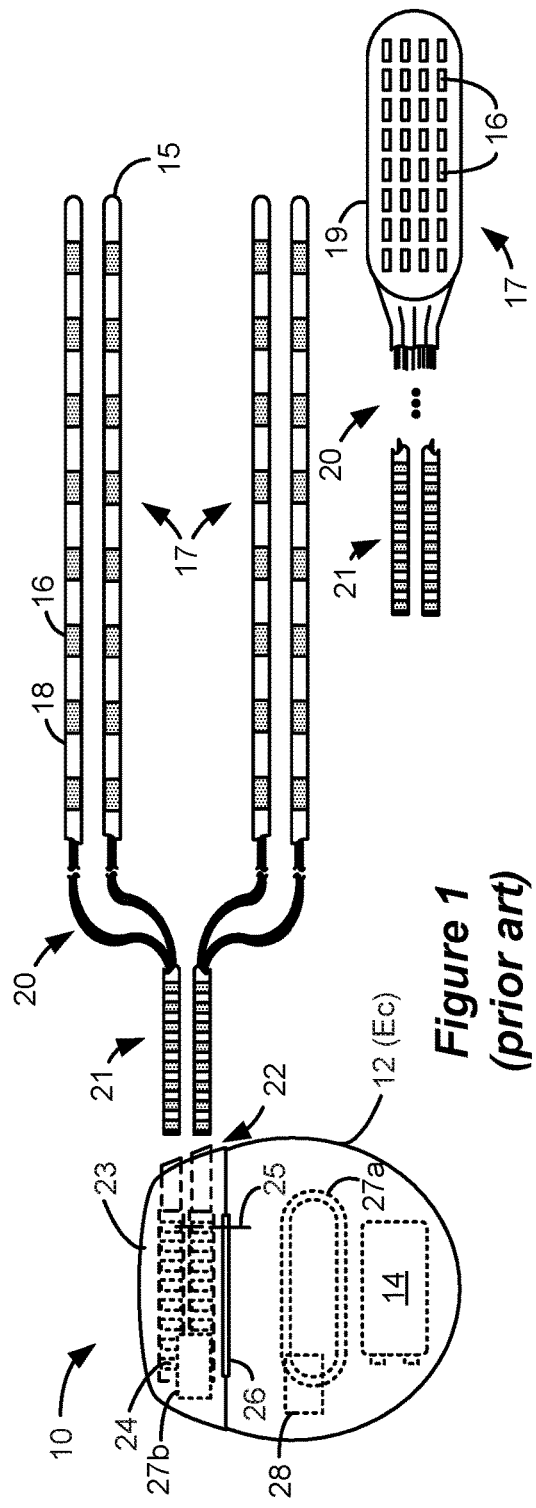
*Figure 1 (prior art)*
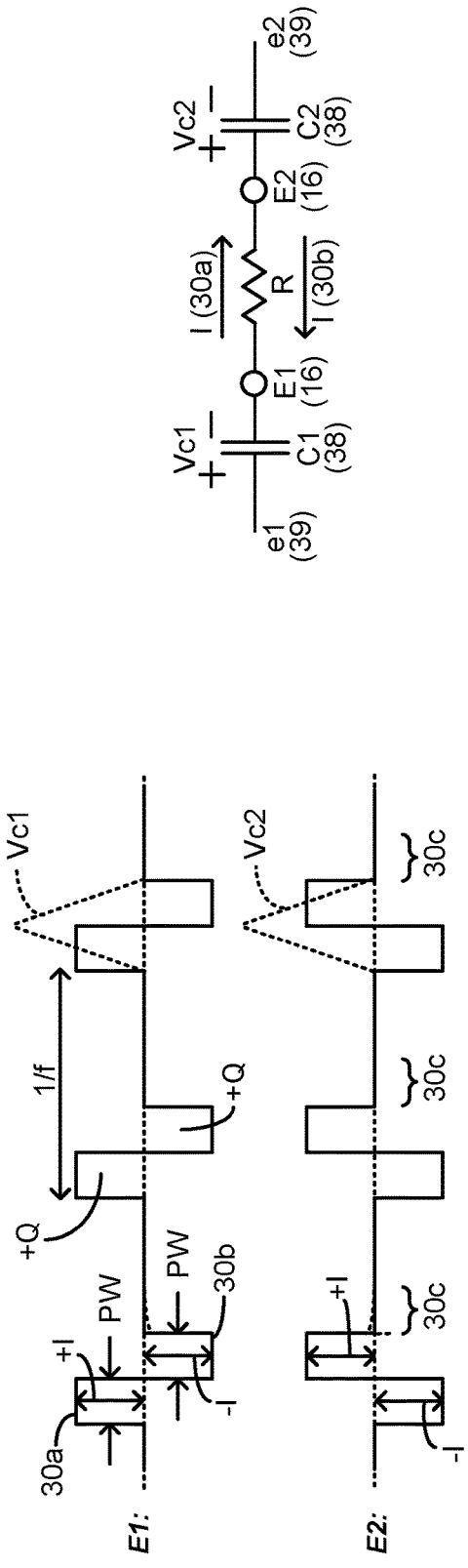
*Figure 2A (prior art)*
*Figure 2B (prior art)*

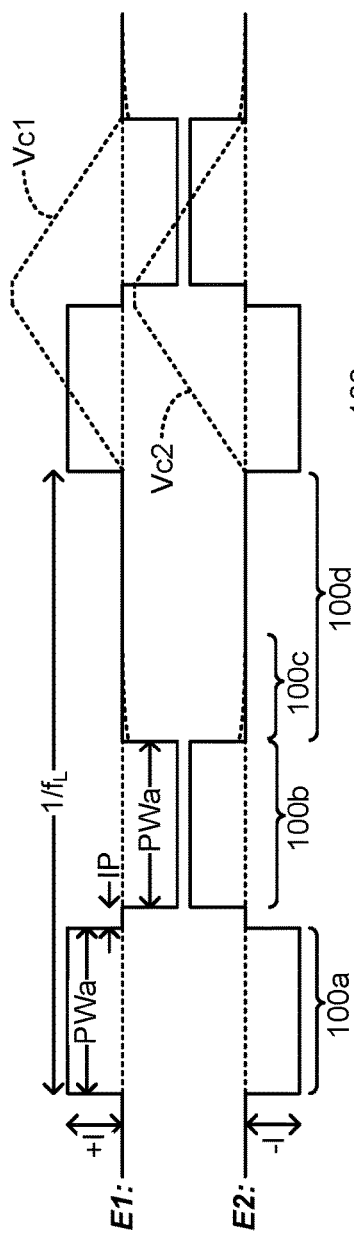
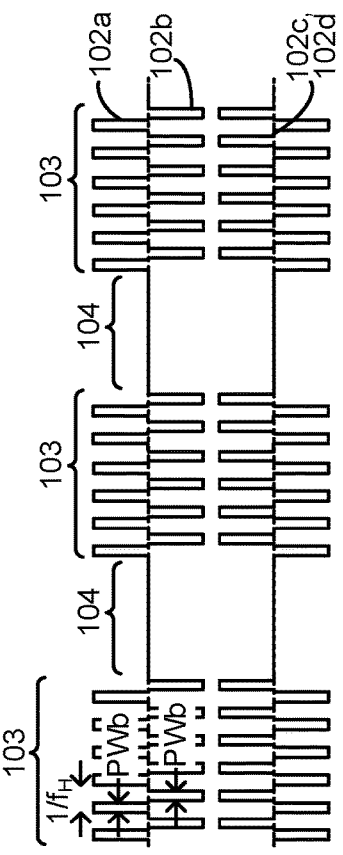
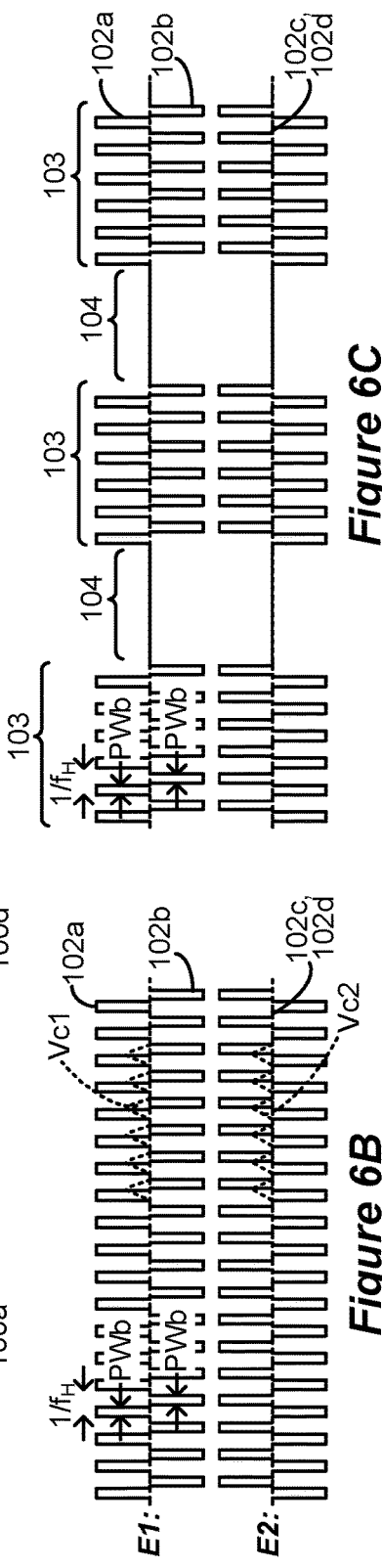
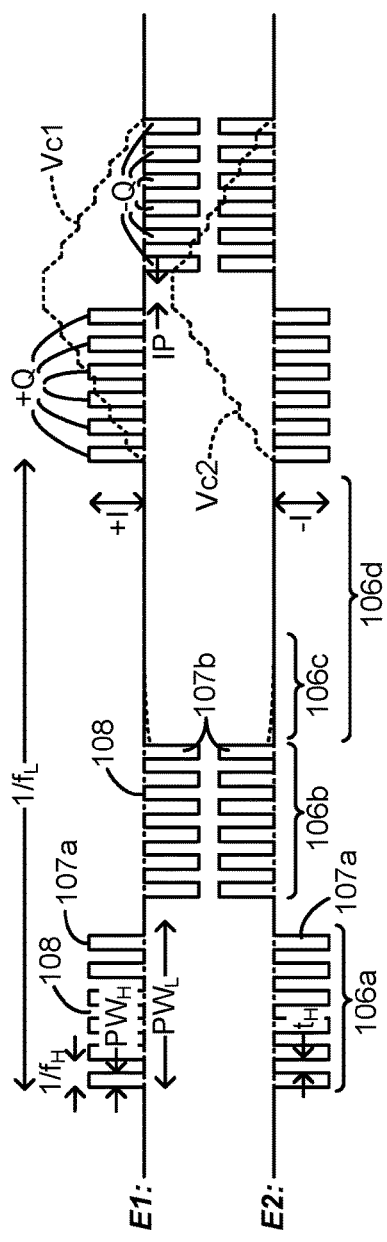

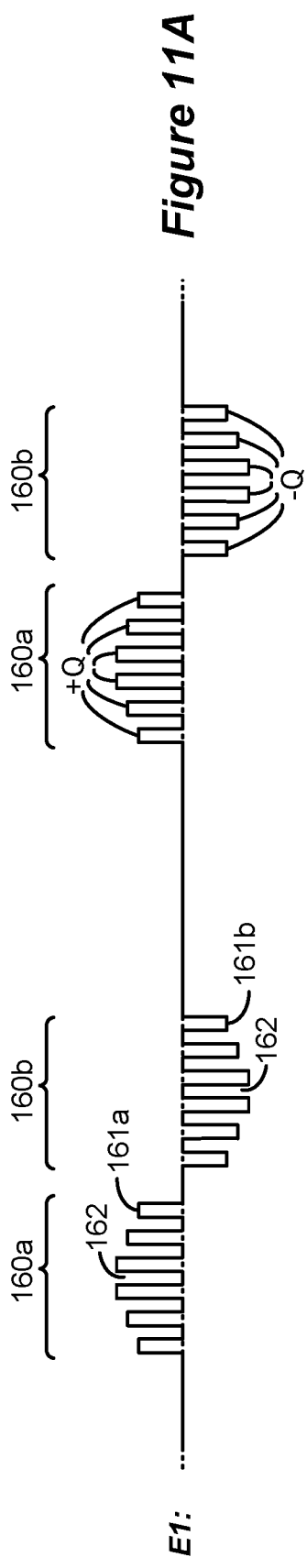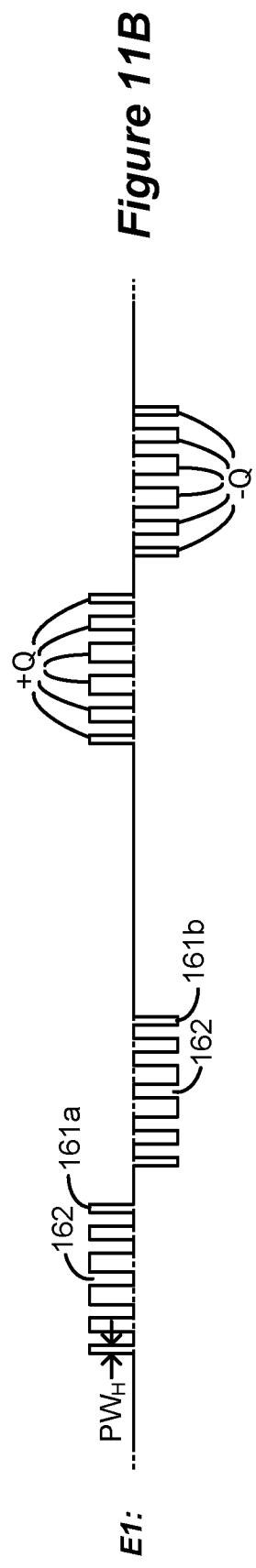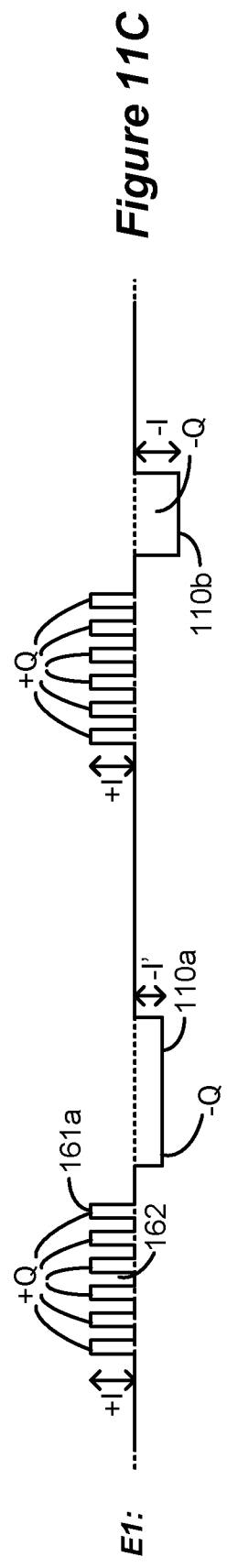

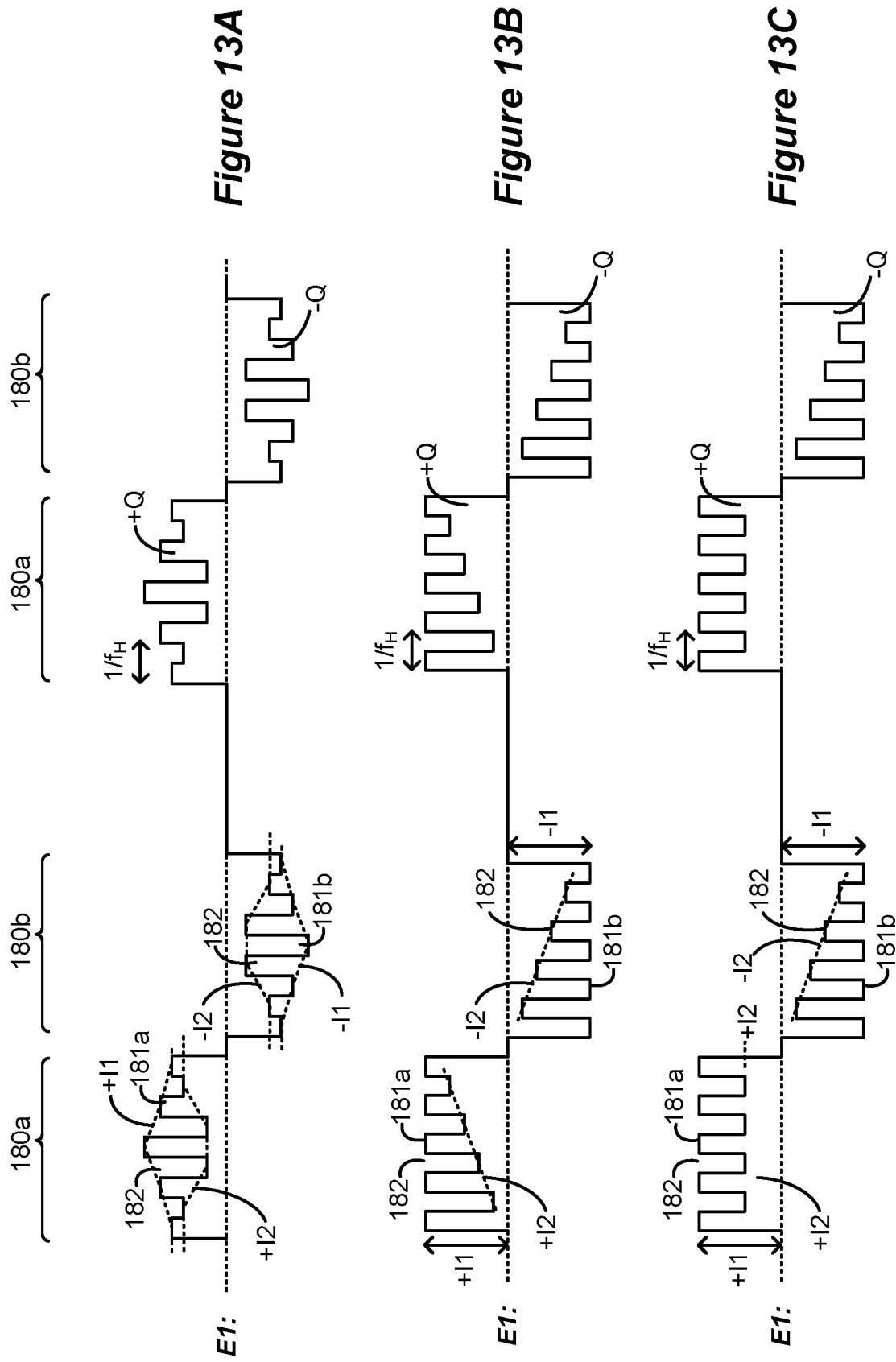

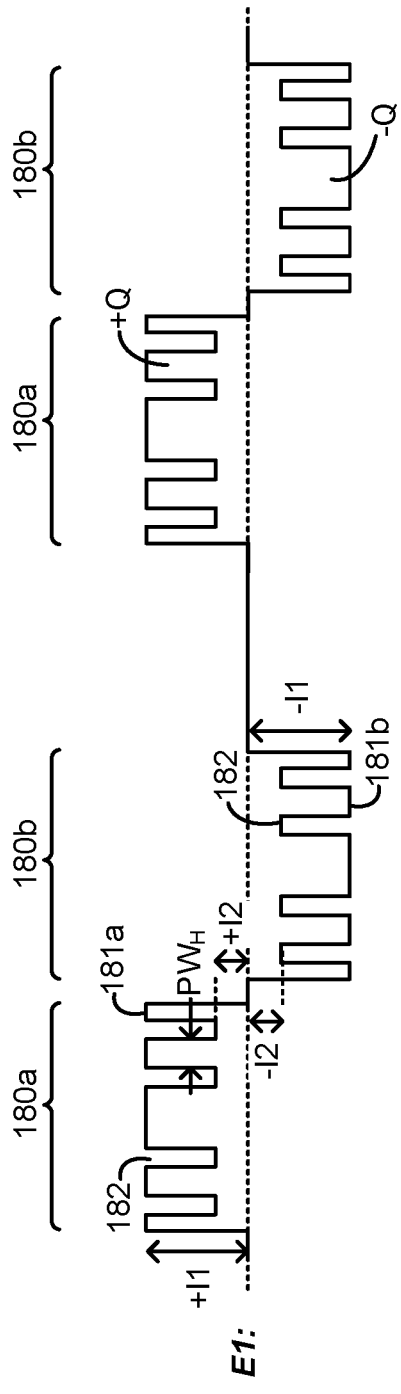
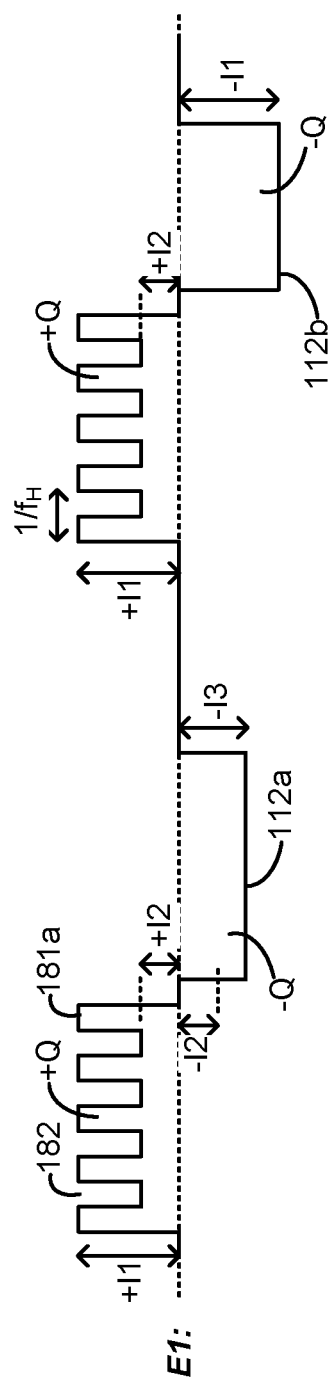
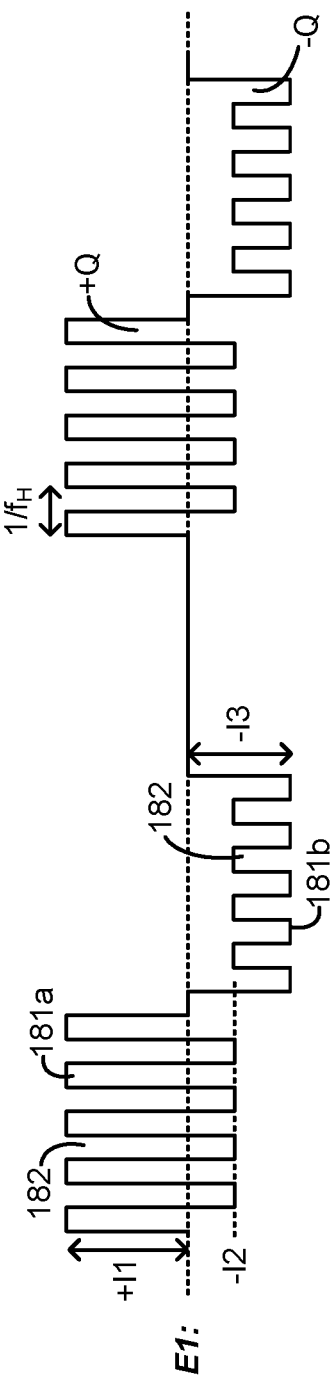

STIMULATION WAVEFORMS WITH HIGH- AND LOW-FREQUENCY ASPECTS IN AN IMPLANTABLE STIMULATOR DEVICE

CROSS REFERENCE TO RELATED APPLICATIONS

This application is a non-provisional application of U.S. Provisional Patent Application Ser. No. 62/670,551, filed May 11, 2018, which is incorporated herein by reference, and to which priority is hereby claimed.

FIELD OF THE INVENTION

This application relates to Implantable Medical Devices (IMDs), and more specifically to circuitry and methods to create high- and low-frequency multiplexed pulses in an implantable stimulator device.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable neurostimulator device system.

An SCS system typically includes an Implantable Pulse Generator (IPG) 10 shown in FIG. 1. The IPG 10 includes a biocompatible device case 12 that holds the circuitry and a battery 14 for providing power for the IPG to function. The IPG 10 is coupled to tissue-stimulating electrodes 16 via one or more electrode leads that form an electrode array 17. For example, one or more percutaneous leads 15 can be used having ring-shaped or split-ring electrodes 16 carried on a flexible body 18. In another example, a paddle lead 19 provides electrodes 16 positioned on one of its generally flat surfaces. Lead wires 20 within the leads are coupled to the electrodes 16 and to proximal contacts 21 insertable into lead connectors 22 fixed in a header 23 on the IPG 10, which header can comprise an epoxy for example. Once inserted, the proximal contacts 21 connect to header contacts 24 within the lead connectors 22, which are in turn coupled by feedthrough pins 25 through a case feedthrough 26 to stimulation circuitry 28 within the case 12, which stimulation circuitry 28 is described below.

In the illustrated IPG 10, there are thirty-two electrodes (E1-E32), split between four percutaneous leads 15, or contained on a single paddle lead 19, and thus the header 23 may include a 2×2 array of eight-electrode lead connectors 22. However, the type and number of leads, and the number of electrodes, in an IPG is application specific and therefore can vary. The conductive case 12 can also comprise an electrode (Ec). In a SCS application, the electrode lead(s) are typically implanted in the spinal column proximate to the dura in a patient's spinal cord, preferably spanning left and right of the patient's spinal column. The proximal contacts 21 are tunneled through the patient's tissue to a distant location such as the buttocks where the IPG case 12 is implanted, at which point they are coupled to the lead connectors 22. In other IPG examples designed for implantation directly at a site requiring stimulation, the IPG can be lead-less, having electrodes 16 instead appearing on the body of the IPG 10. The IPG lead(s) can be integrated with and permanently connected to the IPG 10 in other solutions. The goal of SCS therapy is to provide electrical stimulation from the electrodes 16 to alleviate a patient's symptoms, such as chronic back pain.

IPG 10 can include an antenna 27a allowing it to communicate bi-directionally with a number of external devices discussed subsequently. Antenna 27a as shown comprises a conductive coil within the case 12, although the coil antenna 27a can also appear in the header 23. When antenna 27a is configured as a coil, communication with external devices preferably occurs using near-field magnetic induction. IPG 10 may also include a Radio-Frequency (RF) antenna 27b. In FIG. 1, RF antenna 27b is shown within the header 23, but it may also be within the case 12. RF antenna 27b may comprise a patch, slot, or wire, and may operate as a monopole or dipole. RF antenna 27b preferably communicates using far-field electromagnetic waves, and may operate in accordance with any number of known RF communication standards, such as Bluetooth, Zigbee, WiFi, MICS, and the like.

Stimulation in IPG 10 is typically provided by pulses each of which may include a number of phases such as 30a and 30b, as shown in the example of FIG. 2A. Stimulation parameters typically include amplitude (current I, although a voltage amplitude V can also be used); frequency (f); pulse width (PW) of the pulses or of its individual phases such as 30a and 30b; the electrodes 16 selected to provide the stimulation; and the polarity of such selected electrodes, i.e., whether they act as anodes that source current to the tissue or cathodes that sink current from the tissue. These and possibly other stimulation parameters taken together comprise a stimulation program that the stimulation circuitry 28 in the IPG 10 can execute to provide therapeutic stimulation to a patient.

In the example of FIG. 2A, electrode E1 has been selected as an anode (during its first phase 30a), and thus provides pulses which source a positive current of amplitude +I to the tissue. Electrode E2 has been selected as a cathode (again during first phase 30a), and thus provides pulses which sink a corresponding negative current of amplitude −I from the tissue. This is an example of bipolar stimulation, in which only two lead-based electrodes are used to provide stimulation to the tissue (one anode, one cathode). However, more than one electrode may be selected to act as an anode at a given time, and more than one electrode may be selected to act as a cathode at a given time. Note that at any time the current sourced to the tissue (e.g., +I at E1 during phase 30a) equals the current sunk from the tissue (e.g., −I at E2 during phase 30a) to ensure that the net current injected into the tissue is zero.

IPG 10 as mentioned includes stimulation circuitry 28 to form prescribed stimulation at a patient's tissue. FIG. 3 shows an example of stimulation circuitry 28, which includes one or more current sources 40i and one or more current sinks 42i. The sources and sinks 40i and 42i can comprise Digital-to-Analog converters (DACs), and may be referred to as PDACs 40i and NDACs 42i in accordance with the Positive (sourced, anodic) and Negative (sunk, cathodic) currents they respectively issue. In the example shown, a NDAC/PDAC 40i/42i pair is dedicated (hardwired) to a particular electrode node ei 39. Each electrode node ei 39 is connected to an electrode Ei 16 via a DC-blocking capacitor Ci 38, for the reasons explained below. The stimulation circuitry 28 in this example also supports selection of the conductive case 12 as an electrode (Ec 12), which case electrode is typically selected for monopolar stimulation. In some designs, the case electrode Ec 12 may not have a DC-blocking capacitor 38, and therefore not all potential electrode nodes selected for stimulation may have a DC-blocking capacitor. PDACs 40$i$ and NDACs 42$i$ can also comprise voltage sources.

Proper control of the PDACs 40$i$ and NDACs 42$i$ allows any of the electrodes 16 to act as anodes or cathodes to create a current through a patient's tissue, R, hopefully with good therapeutic effect. In the example shown, electrode E1 has been selected as an anode electrode to source current to the tissue R and E2 as a cathode electrode to sink current from the tissue R. Thus PDAC 40$_1$ and NDAC 42$_2$ are activated and digitally programmed to produce the desired current, I, with the correct timing (e.g., in accordance with the prescribed frequency F and pulse widths PWa and PWb). Power for the stimulation circuitry 28 is provided by a compliance voltage VH, as described in further detail in U.S. Patent Application Publication 2013/0289665. More than one anode electrode and more than one cathode electrode may be selected at one time, and thus current can flow through the tissue R between two or more of the electrodes 16.

Other stimulation circuitries 28 can also be used in the IPG 10. In an example not shown, a switching matrix can intervene between the one or more PDACs 40$i$ and the electrode nodes ei 39, and between the one or more NDACs 42$i$ and the electrode nodes. Switching matrices allows one or more of the PDACs or one or more of the NDACs to be connected to one or more electrode nodes at a given time. Various examples of stimulation circuitries can be found in U.S. Pat. Nos. 6,181,969, 8,606,362, 8,620,436, and U.S. Patent Application Publications 2018/0071520 and 2019/0083796.

Much of the stimulation circuitry 28 of FIG. 3, including the PDACs 40$i$ and NDACs 42$i$, the switch matrices (if present), and the electrode nodes ei 39 can be integrated on one or more Application Specific Integrated Circuits (ASICs), as described in U.S. Patent Application Publications 2012/0095529, 2012/0092031, and 2012/0095519. As explained in these references, ASIC(s) may also contain other circuitry useful in the IPG 10, such as telemetry circuitry (for interfacing off chip with telemetry antennas 27$a$ and/or 27$b$), circuitry for generating the compliance voltage VH, various measurement circuits, etc.

Also shown in FIG. 3 are DC-blocking capacitors Ci 38 placed in series in the electrode current paths between each of the electrode nodes ei 39 and the electrodes Ei 16 (including the case electrode Ec 12). The DC-blocking capacitors 38 act as a safety measure to prevent DC current injection into the patient, as could occur for example if there is a circuit fault in the stimulation circuitry 28. The DC-blocking capacitors 38 are typically provided off-chip (off of the ASIC(s)), and instead may be provided in or on a circuit board in the IPG 10 used to integrate its various components, as explained in U.S. Patent Application Publication 2015/0157861.

Referring again to FIG. 2A, the stimulation pulses as shown are biphasic, with each pulse comprising a first phase 30$a$ followed thereafter by a second phase 30$b$ of opposite polarity. Biphasic pulses are useful to actively recover any charge that might be stored on capacitive elements in the electrode current paths, such as on the DC-blocking capacitors 38. Charge recovery is shown with reference to both FIGS. 2A and 2B. During the first pulse phase 30$a$, charge will build up across the DC-blockings capacitors C1 and C2 associated with the electrodes E1 and E2 used to produce the current, giving rise to voltages Vc1 and Vc2 which increase in accordance with the magnitude of the current and the capacitance of the capacitors 38 (dV/dt=I/C). During the second pulse phase 30$b$, when the polarity of the current I is reversed at the selected electrodes E1 and E2, the stored charge on capacitors C1 and C2 is actively recovered, and thus voltages Vc1 and Vc2 fall and hopefully return to 0V at the end the second pulse phase 30$b$.

To recover all charge by the end of the second pulse phase 30$b$ of each pulse (Vc1=Vc2=0V), the first and second phases 30$a$ and 30$b$ are charged balanced at each electrode, with the first pulse phase 30$a$ providing a charge of +Q and the second pulse phase 30$b$ providing a charge of −Q. In the example shown, such charge balancing is achieved by using the same pulse width (PW) and the same amplitude (|I|) for each of the opposite-polarity pulse phases 30$a$ and 30$b$. However, the pulse phases 30$a$ and 30$b$ may also be charged balance if the product of the amplitude and pulse widths of the two phases 30$a$ and 30$b$ are equal, or if the area under each of the phases is equal, as is known.

FIG. 3 shows that stimulation circuitry 28 can include passive recovery switches 41$i$, which are described further in U.S. Patent Application Publications 2018/0071527 and 2018/0140831. Passive recovery switches 41$i$ may be attached to each of the electrode nodes ei 39, and are used to passively recover any charge remaining on the DC-blocking capacitors Ci 38 after issuance of the second pulse phase 30$b$—i.e., to recover charge without actively driving a current using the DAC circuitry. Passive charge recovery can be prudent, because non-idealities in the stimulation circuitry 28 may lead to pulse phases 30$a$ and 30$b$ that are not perfectly charge balanced. Therefore, and as shown in FIG. 2A, passive charge recovery typically occurs after the issuance of second pulse phases 30$b$, for example during at least a portion 30$c$ of the quiet periods between the pulses, by closing passive recovery switches 41$i$. As shown in FIG. 3, the other end of the switches 41$i$ not coupled to the electrode nodes ei 39 are connected to a common reference voltage, which in this example comprises the voltage of the battery 14, Vbat, although another reference voltage could be used. As explained in the above-cited references, such passive charge recovery tends to equilibrate the charge on the DC-blocking capacitors 38 by placing the capacitors in parallel between the reference voltage (Vbat) and the patient's tissue.

FIG. 4 shows an external trial stimulation environment that may precede implantation of an IPG 10 in a patient. During external trial stimulation, stimulation can be tried on a prospective implant patient without going so far as to implant the IPG 10. Instead, one or more trial electrode arrays 17' (e.g., one or more trial percutaneous leads 15 or trial paddle leads 19) are implanted in the patient's tissue at a target location 52, such as within the spinal column as explained earlier. The proximal ends of the trial electrode array(s) 17' exit an incision 54 in the patient's tissue and are connected to an External Trial Stimulator (ETS) 50. The ETS 50 generally mimics operation of the IPG 10, and thus can provide stimulation to the patient's tissue as explained above. See, e.g., U.S. Pat. No. 9,259,574, disclosing a design for an ETS. The ETS 50 is generally worn externally by the patient for a short while (e.g., two weeks), which allows the patient and his clinician to experiment with different stimulation parameters to hopefully find a stimulation program that alleviates the patient's symptoms (e.g., pain). If external trial stimulation proves successful, the trial electrode array(s) 17' are explanted, and a full IPG 10 and a permanent electrode array 17 (e.g., one or more percutaneous 15 or paddle 19 leads) are implanted as described above; if unsuccessful, the trial electrode array(s) 17' are simply explanted.

Like the IPG 10, the ETS 50 can include one or more antennas to enable bi-directional communications with external devices such as those shown in FIG. 5. Such antennas can include a near-field magnetic-induction coil antenna 56a, and/or a far-field RF antenna 56b, as described earlier. ETS 50 may also include stimulation circuitry 58 (FIG. 4) able to form stimulation in accordance with a stimulation program, which circuitry may be similar to or comprise the same stimulation circuitry 28 (FIG. 3) present in the IPG 10. ETS 50 may also include a battery (not shown) for operational power.

FIG. 5 shows various external devices that can wirelessly communicate data with the IPG 10 or ETS 50, including a patient, hand-held external controller 60, and a clinician programmer 70. Both of devices 60 and 70 can be used to wirelessly transmit a stimulation program to the IPG 10 or ETS 50—that is, to program their stimulation circuitries 28 and 58 to produce stimulation with a desired amplitude and timing described earlier. Both devices 60 and 70 may also be used to adjust one or more stimulation parameters of a stimulation program that the IPG 10 is currently executing. Devices 60 and 70 may also wirelessly receive information from the IPG 10 or ETS 50, such as various status information, etc.

External controller 60 can be as described in U.S. Patent Application Publication 2015/0080982 for example, and may comprise a controller dedicated to work with the IPG 10 or ETS 50. External controller 60 may also comprise a general purpose mobile electronics device such as a mobile phone which has been programmed with a Medical Device Application (MDA) allowing it to work as a wireless controller for the IPG 10 or ETS, as described in U.S. Patent Application Publication 2015/0231402. External controller 60 includes a user interface, preferably including means for entering commands (e.g., buttons or selectable graphical elements) and a display 62. The external controller 60's user interface enables a patient to adjust stimulation parameters, although it may have limited functionality when compared to the more-powerful clinician programmer 70, described shortly.

The external controller 60 can have one or more antennas capable of communicating with the IPG 10. For example, the external controller 60 can have a near-field magnetic-induction coil antenna 64a capable of wirelessly communicating with the coil antenna 27a or 56a in the IPG 10 or ETS 50. The external controller 60 can also have a far-field RF antenna 64b capable of wirelessly communicating with the RF antenna 27b or 56b in the IPG 10 or ETS 50.

Clinician programmer 70 is described further in U.S. Patent Application Publication 2015/0360038, and can comprise a computing device 72, such as a desktop, laptop, or notebook computer, a tablet, a mobile smart phone, a Personal Data Assistant (PDA)-type mobile computing device, etc. In FIG. 5, computing device 72 is shown as a laptop computer that includes typical computer user interface means such as a screen 74, a mouse, a keyboard, speakers, a stylus, a printer, etc., not all of which are shown for convenience. Also shown in FIG. 5 are accessory devices for the clinician programmer 70 that are usually specific to its operation as a stimulation controller, such as a communication "wand" 76 coupleable to suitable ports on the computing device 72, such as USB ports 79 for example.

The antenna used in the clinician programmer 70 to communicate with the IPG 10 or ETS 50 can depend on the type of antennas included in those devices. If the patient's IPG 10 or ETS 50 includes a coil antenna 27a or 56a, wand 76 can likewise include a coil antenna 80a to establish near-filed magnetic-induction communications at small distances. In this instance, the wand 76 may be affixed in close proximity to the patient, such as by placing the wand 76 in a belt or holster wearable by the patient and proximate to the patient's IPG 10 or ETS 50. If the IPG 10 or ETS 50 includes an RF antenna 27b or 56b, the wand 76, the computing device 72, or both, can likewise include an RF antenna 80b to establish communication at larger distances. The clinician programmer 70 can also communicate with other devices and networks, such as the Internet, either wirelessly or via a wired link provided at an Ethernet or network port.

To program stimulation programs or parameters for the IPG 10 or ETS 50, the clinician interfaces with a clinician programmer graphical user interface (GUI) 82 provided on the display 74 of the computing device 72. As one skilled in the art understands, the GUI 82 can be rendered by execution of clinician programmer software 84 stored in the computing device 72, which software may be stored in the device's non-volatile memory 86. Execution of the clinician programmer software 84 in the computing device 72 can be facilitated by control circuitry 88 such as one or more microprocessors, microcomputers, FPGAs, DSPs, other digital logic structures, etc., which are capable of executing programs in a computing device, and which may comprise their own memories. For example, control circuitry 88 can comprise an i5 processor manufactured by Intel Corp, as described at https://www.intel.com/content/www/us/en/products/processors/core/i5-processors.html. Such control circuitry 88, in addition to executing the clinician programmer software 84 and rendering the GUI 82, can also enable communications via antennas 80a or 80b to communicate stimulation parameters chosen through the GUI 82 to the patient's IPG 10.

The user interface of the external controller 60 may provide similar functionality because the external controller 60 can include the same hardware and software programming as the clinician programmer. For example, the external controller 60 includes control circuitry 66 similar to the control circuitry 88 in the clinician programmer 70, and may similarly be programmed with external controller software stored in device memory.

SUMMARY

In a first example, a stimulator device is disclosed which may comprise: a plurality of electrode nodes, each electrode node configured to be coupled to one of a plurality of electrodes configured to contact a patient's tissue; and stimulation circuitry configured to provide in a single timing channel a sequence of pulses at at least two of the electrode nodes selected to create a stimulation current through the patient's tissue, wherein the stimulation circuitry is configured to form each pulse at the selected electrode nodes with a first phase and a second phase, wherein the first phase at each selected electrode node comprises a plurality of first monophasic sub-phase pulses of a first polarity and separated by gaps during which no current is issued to the tissue, wherein the second phase at each selected electrode node comprises a plurality of second monophasic sub-phase pulses of a second polarity opposite the first polarity and separated by gaps during which no current is issued to the tissue, and wherein at each selected electrode node a first total charge of the plurality of first monophasic sub-phase pulses is equal but opposite a second total charge of the plurality of second monophasic sub-phase pulses.

The stimulator device may further comprise a case for housing the stimulation circuitry, wherein the case is conductive, and wherein the conductive case comprises one of the plurality of electrodes. At least one selected electrode node may be coupled to its associated electrode through a DC-blocking capacitor. The stimulator device may further comprise at least one implantable lead, wherein the electrodes are located on the lead.

Each first and second monophasic sub-phase pulse may be of a constant amplitude, which may comprises a constant current. An amplitude of the first monophasic sub-phase pulses may vary during the first pulse phase, or an amplitude of the second monophasic sub-phase pulses may vary during the second pulse phase. The amplitude of the first monophasic sub-phase pulses may vary during the first pulse phase and the amplitude of the second monophasic sub-phase pulses may vary during the second pulse phase. A pulse width of the first monophasic sub-phase pulses may vary during the first pulse phase, or a pulse width of the second monophasic sub-phase pulses may vary during the second pulse phase. The pulse width of the first monophasic sub-phase pulses may varies during the first pulse phase and the pulse width of the second monophasic sub-phase pulses may vary during the second pulse phase. A frequency of the first monophasic sub-phase pulses may vary during the first pulse phase, or a frequency of the second monophasic sub-phase pulses may vary during the second pulse phase. The frequency of the first monophasic sub-phase pulses may vary during the first pulse phase and the frequency of the second monophasic sub-phase pulses may vary during the second pulse phase.

The stimulator device may further comprise control circuitry, wherein the control circuitry is configured to receive a plurality of stimulation parameters including a first frequency of the pulses, a second frequency of the first and second monophasic sub-phase pulses, a pulse width of at least one of the first and second phases, and a pulse width of the first and second monophasic pulses, and the control circuitry may be configured to use the stimulation parameters to provide a plurality of control signals to the stimulation circuitry to cause the stimulation circuitry to form the sequence of pulses at the selected electrode nodes. The stimulator device may further comprise an antenna, wherein the control circuitry is configured to receive the stimulation parameters from the antenna. The control circuitry may be configured to produce a first digital signal at the second frequency, a second digital signal at the first frequency and corresponding to a timing of the first phase, and a third digital signal at the first frequency and corresponding to a timing of the second phase. The stimulation circuitry may comprise a plurality of switches, wherein the plurality of switches are controlled by a mixture of the first and second digital signals during the first phase, and wherein the plurality of switches are controlled by a mixture of the first and third digital signals during the second phase.

The stimulator device may comprise an implantable pulse generator or an external stimulator.

The stimulation circuitry may be configured to form an interphase period at the selected electrode nodes between the first phase and the second phase, wherein no current is issued to the tissue during the interphase period.

The first monophasic sub-phase pulses may be positive at at least one of the selected electrode nodes and negative at at least one other of the selected electrode nodes such that the net current injected into the tissue at any time is zero during the first phase, and the second monophasic sub-phase pulses may be negative at the at least one of the selected electrode nodes and positive at the at least one other of the selected electrode nodes such that the net current injected into the tissue at any time is zero during the second phase.

In a second example, a stimulator device is disclosed which may comprise: a plurality of electrode nodes, each electrode node configured to be coupled to one of a plurality of electrodes configured to contact a patient's tissue; and stimulation circuitry configured to provide a sequence of pulses at at least two of the electrode nodes selected to create a stimulation current through the patient's tissue, wherein the stimulation circuitry is configured to form each pulse at the selected electrode nodes with a first phase and a second phase, wherein one of the first or second phases at each selected electrode node comprises a plurality of monophasic sub-phase pulses of a first polarity and separated by first gaps, wherein a non-zero current of the first polarity is provided during the first gaps, wherein at each selected electrode node a first total charge of the plurality of monophasic sub-phase pulses plus the non-zero current is equal but opposite a second total charge of the second phase.

The stimulator device may further comprising a case for housing the stimulation circuitry, wherein the case is conductive, and wherein the conductive case comprises one of the plurality of electrodes. At least one selected electrode node may be coupled to its associated electrode through a DC-blocking capacitor. The stimulator device may further comprise at least one implantable lead, wherein the electrodes are located on the lead.

Each monophasic sub-phase pulses may be of a constant amplitude, which may comprise a constant current. The other of the first or second phases at each selected electrode node may comprise a plurality of monophasic sub-phase pulses of a second polarity opposite the first polarity and separated by second gaps, wherein a non-zero current of the second polarity is provided during the second gaps.

The other of the first or second phases at each selected electrode node may comprise a constant pulse.

An amplitude of the monophasic sub-phase pulses may vary during the one of the first or second phases. The non-zero current provided during the first gaps may be constant during the one of the first or second phases. The non-zero current provided during the first gaps may also vary during the one of the first or second phases. A pulse width of the monophasic sub-phase pulses may vary during the one of the first or second phases. A frequency of the monophasic sub-phase pulses may vary during the one of the first or second phases.

The stimulator device may further comprise control circuitry, wherein the control circuitry is configured to receive stimulation parameters including a first frequency of the pulses, a second frequency of the monophasic sub-phase pulses, a pulse width of at least one of the first and second phases, and a pulse width of the monophasic pulses, wherein the control circuitry is configured to use the stimulation parameters to provide a plurality of control signals to the stimulation circuitry to cause the stimulation circuitry to form the sequence of pulses at the selected electrode nodes. The stimulator device may further comprise an antenna, wherein the control circuitry is configured to receive the stimulation parameters from the antenna.

The stimulator device may comprises an implantable pulse generator or an external stimulator.

The stimulation circuitry may be configured to form an interphase period at the selected electrode nodes between the first phase and the second phase, wherein no current is issued to the tissue during the interphase period.

The monophasic sub-phase pulses may be positive at at least one of the selected electrode nodes and negative at at least one other of the selected electrode nodes such that the net current injected into the tissue at any time is zero during the one of the first or second phases.

The stimulation circuitry may be configured to provide the sequence of pulses in a single timing channel.

In a third example, a stimulator device is disclosed, which may comprise: a plurality of electrode nodes, each electrode node configured to be coupled to one of a plurality of electrodes configured to contact a patient's tissue; and stimulation circuitry configured to provide in a single timing channel a sequence of pulses at at least two of the electrode nodes selected to create a stimulation current through the patient's tissue, wherein the stimulation circuitry is configured to form each pulse at the selected electrode nodes with a first phase and a second phase, wherein the first phase at each selected electrode node comprises a plurality of first monophasic sub-phase pulses of a first polarity and separated by first gaps, wherein the second phase at each selected electrode node comprises a plurality of second monophasic sub-phase pulses of a second polarity opposite the first polarity and separated by second gaps, and wherein at each selected electrode node a first total charge of the first phase is equal but opposite a second total charge of the second phase.

No current may be issued to the current during the first and second gaps. A non-zero current of the first polarity may be provided during the first gaps, and a non-zero current of the second polarity may be provided during the second gaps. Alternatively, a non-zero current of the same polarity may be provided during the first and second gaps, and the non-zero current may have the same amplitude during the first and second gaps.

BRIEF DESCRIPTION OF THE DRAWINGS

FIG. 1 shows an Implantable Pulse Generator (IPG), in accordance with the prior art.

FIGS. 2A and 2B show an example of stimulation pulses (waveforms) producible by the IPG or by an External Trial Stimulator (ETS), in accordance with the prior art.

FIGS. 6A-6C show biphasic waveforms producible by the IPG or ETS at low and high frequencies, and in pulse packets.

FIG. 7 shows a first example of waveforms producible by the IPG or ETS at electrodes and having both low- and high-frequency aspects in accordance with the invention, having charge-balanced first and second pulse phases, in which each pulse phase is comprised of high-frequency monophasic sub-pulses.

FIGS. 11A-11C show variations to the waveforms of FIG. 7.

FIGS. 13A-13F show variations to the waveforms of FIGS. 12A and 12B.

DETAILED DESCRIPTION

Figure 3:
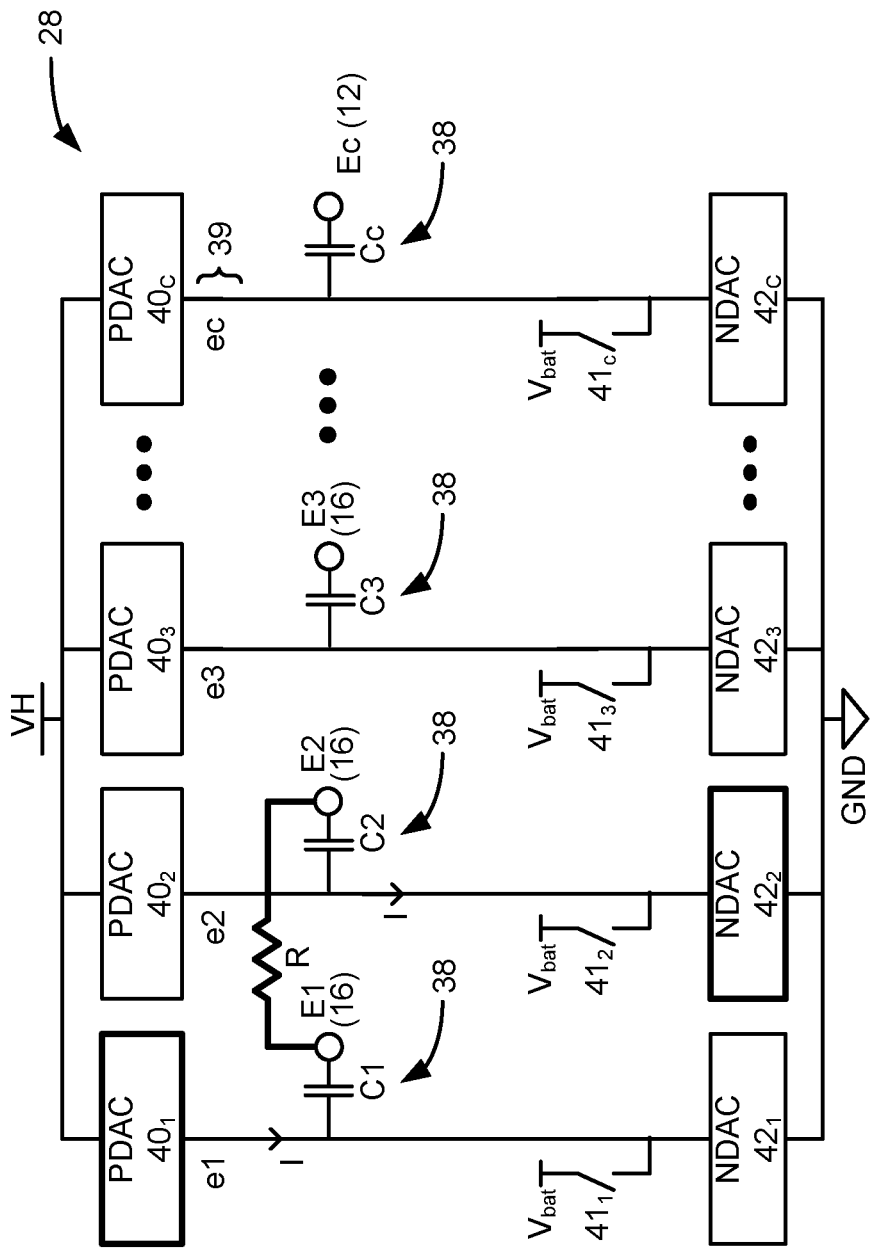
FIG. 3 shows an example of stimulation circuitry useable in the IPG or ETS, in accordance with the prior art.
Figure 4:
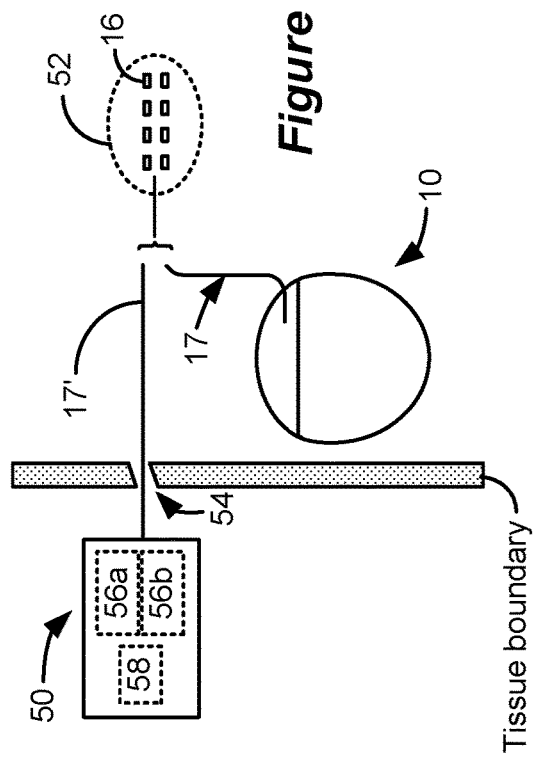
FIG. 4 shows an ETS environment useable to provide stimulation before implantation of an IPG, in accordance with the prior art.

Traditionally, pain relief in Spinal Cord Stimulation (SCS) systems was achieved by using a sequence of pulses operating at a relatively low frequency, $f_L$, as shown in FIG. 6A. FIG. 6A shows a stimulation program essentially similar to that illustrated in FIG. 2A, in which biphasic pulses with phases 100a and 100b are used to create a current I between any electrodes (e.g., E1 and E2) selected from the plurality of electrodes. Here it is assumed that the duration PWa of both phases 100a and 100b of the pulses are the same as well as their amplitudes I for balanced active charge recovery, although these pulse widths/amplitudes can differ while still achieving charge-balanced phases, as explained earlier. Also shown is an interphase period (IP) between the phases 100a and 100b in each pulse, during which no current is provided; this is useful to provide time to allow switching in the stimulation circuitry 28/58 in the IPG or ETS to stabilize after exiting a first pulse phase 100a and before entering the second pulse phase 100b. Further shown are the passive charge recovery periods 100c that can occur during quiet periods 100d when passive recovery switches 41i (FIG. 3) can be closed, again as explained earlier. Generally speaking, the low frequency $f_L$ of the pulses in FIG. 6A can comprise 200 Hz or less.

The use of lower-frequency pulses for spinal cord stimulation has been reported by patients, in addition to pain relief, to sometimes cause paresthesia, i.e., a tickling, prickling, or temperature-change sensation. While some patients don't mind, or may actually enjoy, the feeling of paresthesia, other patients would prefer to not feel paresthesia. High-frequency stimulation has been reported as helpful in reducing paresthesia perhaps to sub-threshold levels, as shown in FIG. 6B. Here, biphasic pulses with charge-balanced phases 102a and 102b are issued at a higher frequency $f_H$, which can comprise 2000 Hz or greater. Because the pulses are issued at a high frequency, their pulse widths are generally smaller as well, and in FIG. 6B a single pulse width PWb is shown for both of the phases 102a and 102b, although again this is not strictly necessary as charge balance between the phases can be achieved in different manners.

While high-frequency pulses such as those shown in FIG. 6B may be helpful in reducing or eliminating paresthesia, such pulses also present implementation challenges in an IPG 10 or ETS 50. First, the quiet period 102d between the pulses—i.e., after a second pulse phase 102b and before a next first pulse phase 102a—is short. This can make use of passive charge recovery during periods 102c difficult or ineffective, either because there is not enough time to close the passive recovery switches 41i (FIG. 3), or because the time period during which those switches can be closed is not long enough to allow the DC-blocking capacitors 38 (FIG. 3) to equilibrate charge that may be stored on them. See, e.g., U.S. patent application Ser. No. 15/799,499, filed Oct. 31, 2017, discussing this problem in further detail.

Second, it can also be difficult to accommodate a significant interphase period (IP) between each of pulses phases 102a and 102b, because again there may not be sufficient time to implement such a period. This can make switching in the stimulation circuitry 28/58 difficult, and can lead to unwanted ringing in the pulse phases.

High-frequency pulses as shown in FIG. 6B also require more power to produce. As one skilled in the art will appreciate, higher-frequency pulses require more frequent switching in the stimulation circuitry 28/58 used to form the pulses. This leads to higher power consumption compared to lower-frequency pulses that require less frequent switching, even if the time-average of the current is the same for the lower and higher frequency pulses (e.g., if they have the same on/off duty cycle). This is especially problematic for an IPG 10 powered by a battery 14, which is implanted and cannot be changed. High-frequency pulses will cause a permanent battery 14 to deplete more quickly, which could require explantation of the IPG 10 before its useful life is otherwise spent. If the battery 14 is rechargeable, high-frequency pulses will require more frequent external (wireless) charging of the battery, possibly to a point where such charging becomes inconvenient or is impractical. The need to more frequently externally charge a rechargeable battery 14 also accelerates the battery's degradation, again running the risk of the need for a premature explantation.

In FIG. 6B, the high-frequency biphasic pulses are free running, effectively issuing without cessation over some therapeutic time period. One manner of mitigating increased power consumption when using high-frequency pulses is to issue such pulses in packets 103, as shown in FIG. 6C. As shown, a number of biphasic pulses pulse of high frequency $f_H$ are issued in each packet 103, with each packet 103 being followed by a period 104 of no current (stimulation). This reduces power consumption, both because the time-averaged current is reduced (no current issues during periods 104), and because the number of times the stimulation circuitry 28/58 must be switched is reduced. However, it can still be difficult to provide passive charge recovery 102c during the quiet 102d periods between the biphasic pulses in each packet 103, and again it is difficult to provide a significant interphase period (IP) to assist with switching between pulse phases 102a and 102b.

To remedy these problems while still providing reduced paresthesia (sub-threshold) stimulation to a patient, new stimulation waveforms, and methods and circuitry for producing them, are disclosed having both low-frequency ($f_L$) and high-frequency ($f_H$) features. A first example of such a waveform is shown in FIG. 7. FIG. 7 shows a sequence of pulses, with each pulse comprising a first phase 106a followed by a second phase 106b. These pulses are issued at a low frequency $f_L$, similar to the pulses of FIG. 6A. The duration $PW_L$ of each of pulse phases 106a and 106b may equal the duration PWa of the pulse phases 100a and 100b of the low-frequency biphasic pulses of FIG. 6A, but this is not strictly necessary.

Each pulse phase 106a and 106b is fractionalized into sub-phase pulses 107a and 107b. Each of the sub-phase pulses 107a and 107b are issued at a high frequency $f_H$, similar to the high frequency at which the biphasic pulses are issued in FIGS. 6B and 6C. Notice however that the sub-phase pulses 107a and 107b are monophasic, not biphasic. Thus, at electrode E1, each sub-phase pulse 107a is only positive during first pulse phases 106a, and each sub-phase pulse 107b is only negative during second pulse phases 106b. At electrode E2 the polarity is reversed, such that each sub-phase pulse 107a is only negative during first pulse phases 106a, and each sub-phase pulse 107b is only positive during second pulse phases 106b.

In the illustrated example, each of the sub-phase pulses 107a and 107b has the same amplitude +I or −I and the same pulse width $PW_H$. Note that at any time the current sourced to the tissue (e.g., +I at E1 during sub-phase pulses 107a) equals the current sunk from the tissue (e.g., −I at E2 during sub-phase pulses 107a) to ensure that the net current injected into the tissue at any time is zero.

The pulse width $PW_H$ of the sub-phase pulses 107a and 107b may equal the duration of either of the pulse phases 102a or 102b (e.g., PWb), or of the total duration of both phases (e.g., 2 PWb), of the high-frequency biphasic pulses shown in FIGS. 6B and 6C. However, this is not strictly necessary.

The sub-phase pulses 107a and 107b are separated by gaps 108 of duration $t_H$, during which, in one example, no stimulation current occurs. The duration $t_H$ of gaps 108 may equal the duration of the quiet periods 102d between the high-frequency biphasic pulses shown in FIGS. 6B and 6C, but again this is not strictly necessary. The duration of the sub-phase pulses 107a and 107b ($PW_H$) may equal the duration of the gaps 108 ($t_H$) as shown, but again this is not necessary.

In a preferred example, the total charge provided by first pulse phase 106a at each electrode equals the opposite total charge provided by the second pulse phase 106b. In other words, the total charge +Q provided by the sub-phase pulses 107a of the first pulse phase 106a at electrode E1 equals the opposite total charge −Q provided by the sub-phase pulses 107b of the second pulse phase 106b at electrode E1, and likewise for electrode E2 but with the charge polarity reversed. This provides charge balance to the pulses at each electrode.

Notice that while the sub-phase pulses 107a and 107b are issued at a high frequency $f_H$, the fact that they are not biphasic means that the number of times the stimulation circuitry 28/58 must be switched is reduced. For example, and by comparison to the high frequency biphasic pulses of FIGS. 6B and 6C, the frequency of switching can be reduced by half: whereas each high-frequency biphasic pulse at an electrode must switch on, then off (assuming an interphase period is used), then to the opposite polarity, then off, each sub-phase pulse 107a or 107b will only switch on and then off during the same duration. This saves power, and is thus more considerate of the IPG or ETS battery.

As shown in FIG. 7, an interphase period (IP) may intervene between the first and second pulse phases 106a and 106b, and passive recovery may (closing of switches 41i; FIG. 3) occur during periods 106c following the second pulse phases 106b, which periods 106c can occur for at least a portion of quiet periods 106d between the pulses. The duration of the passive recovery periods 106c may equal the duration of similar periods 100c in the low-frequency pulses of FIG. 6A, although this isn't necessary. Likewise, the quiet periods 106d between the pulses may equal the duration of the similar periods 106d in the low-frequency pulses of FIG. 6A, or may equal the duration 104 between the packets 103 of high-frequency pulses in FIG. 6C, although again this isn't necessary. Unlike the high-frequency biphasic pulses used in FIGS. 6B and 6C, the low-frequency, longer-time-scale aspects of the waveforms of FIG. 7 provide ample time to accommodate the interphase period (IP) and passive recovery during periods 106c.

While the pulses of FIG. 7 desirably provide aspects of high-frequency paresthesia-free stimulation, they behave like low frequency pulses from a charge injection standpoint. This is illustrated by reviewing the manner in which charge accumulates on the DC-blocking capacitors 38 (FIG. 3) during each of the pulses (Vc1, Vc2). For the low-frequency pulses of FIG. 6A, and as already explained (FIG. 2A), charge accumulates on the capacitors during the first pulse phases 100a (Vc1 and Vc2 increase) and is actively recovered during the second pulse phases 100b (as Vc1 and Vc2 decrease back to zero). For the high-frequency pulses of FIGS. 6B and 6C, essentially the same process occurs, but on a faster time scale due to the higher-frequency bi-phasic pulses.

For the pulses of FIG. 7, charge is injected during each sub-phase pulse 107a during the first pulse phases 106a, causing Vc1 and Vc2 to increase. Vc1 and Vc2 remain constant (or may slightly decay) during the gaps 108 when no current is provided. Charge is then actively recovered during each sub-phase pulse 107b during each second pulse phase 106b, causing Vc1 and Vc2 to decrease (except during the gaps 108) and return to zero at the end of the second pulse phase 106b. Notice that the overall charge injection profile in FIG. 7 as evidenced by Vc1 and Vc2 is similar in shape to, and occurs on the same time scale as, the low-frequency pulses of FIG. 6A. This is preferable to the higher-frequency charge injection that occurs in the high-frequency pulses of FIGS. 6B and 6C. As explained in the '499 Application referenced above, the short time scales of high-frequency biphasic pulses can make charge recovery difficult.

Preferably the waveforms of FIG. 7 are formed in a single timing channel, i.e., with each of the sub-phase pulses 107a and 107b at an electrode being defined and formed in a single timing channel. This is different, and more convenient, than forming some of the sub-phase pulses 107a and 107b in different timing channels and combining them at the electrode, as described in U.S. Pat. No. 9,358,391 for example. Plus, forming the sub-phase pulses in a single timing channel frees the other timing channels in the IPG or ETS, which may now be used to provide pulses at different electrodes, therefore allowing more complex therapies to be provided to the patient. Use of timing channels in an IPG is discussed further in U.S. Pat. Nos. 6,516,227 and 9,656,081, which are incorporated herein by reference.

Figure 5:
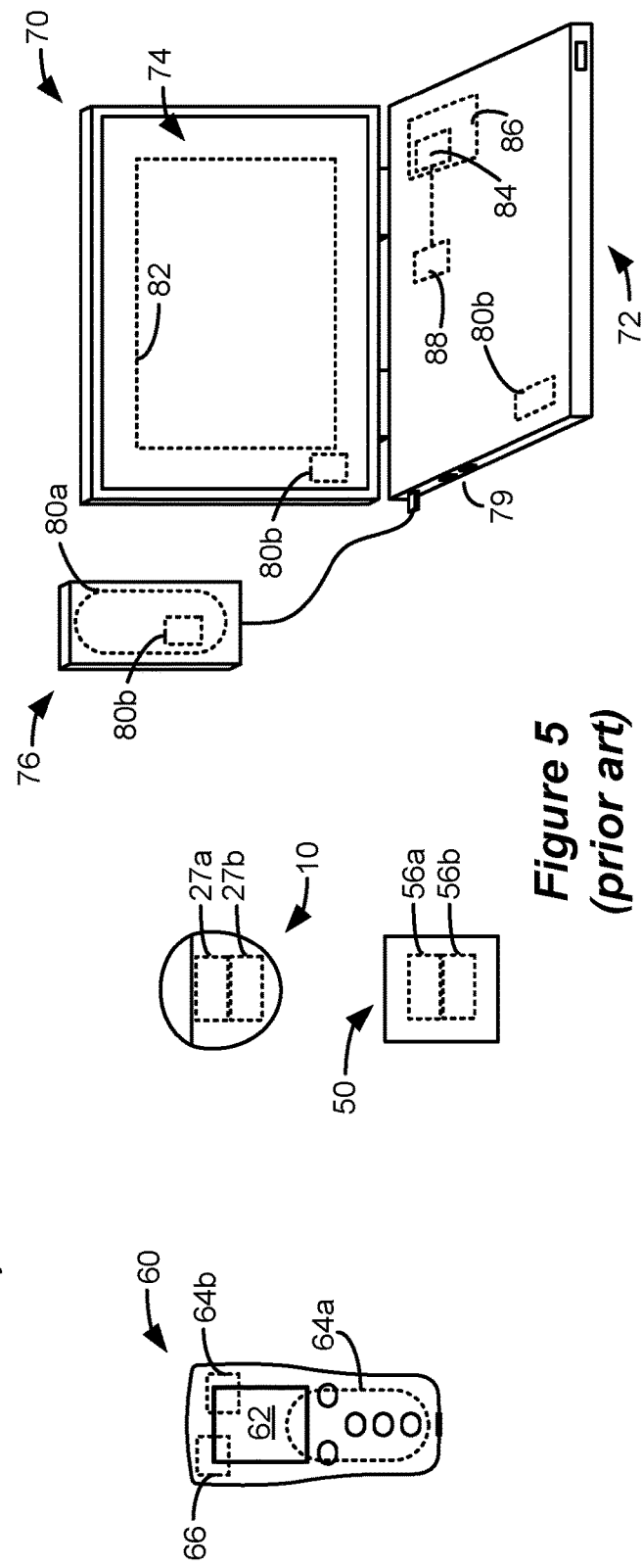
FIG. 5 shows various external devices capable of communicating with and programming stimulation in an IPG or ETS, in accordance with the prior art.
Figure 8:
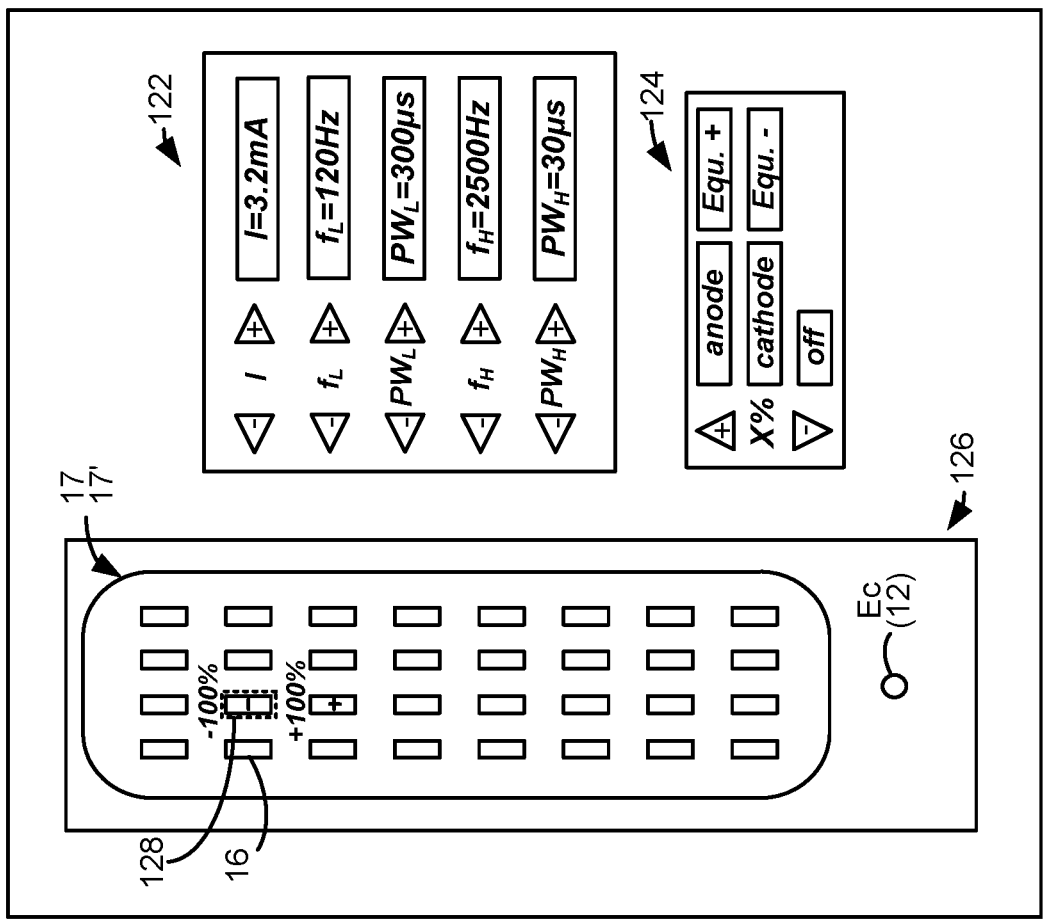
FIG. 8 shows a Graphical User Interface (GUI) of an external device in communication with the IPG or ETS, including settings to allow for programming stimulation parameters for the waveforms of FIG. 7.

FIG. 8 shows a Graphical User Interface (GUI) 120 which can be used to program an IPG 115 to provide the pulses of FIG. 7. GUI 120 may be provided on an external device, such as the external controller 60 or clinician programmer 70 of FIG. 5. One skilled in the art will understand that the particulars of the GUI 120 will depend on where the external device's software is in its execution, which may depend on the GUI selections the clinician or patient has previously made. The instructions for GUI 120 can be stored on a non-transitory computer readable media, such as a solid state, optical, or magnetic memory, and loaded into the relevant external device.

FIG. 8 shows the GUI 120 at a point allowing for the manual setting of stimulation parameters for the patient. A stimulation parameters interface 122 is provided in which specific stimulation parameters can be defined for a stimulation program. Adjustable settings for stimulation parameters are shown, including the amplitude I of the stimulation pulses, and, as particularly relevant to the pulses of FIG. 7, settings to adjust the low ($f_L$) and high ($f_H$) frequency aspects of the pulses. Pulse widths $PW_L$ and $PW_H$ are also provided to set the duration of the pulse phases 106a/106b and the duration of each of the sub-pulse phases 107a/107b respectively. GUI 120 assumes for simplicity that $PW_L$ will be the same for each of the pulse phases 106a and 106b and that and $PW_H$ will be the same for the sub-phase pulses 107a and 107b, but this isn't necessary, and instead means can be provided to allow these parameters to be set separately. The duration $t_H$ of the gaps 108 could also be made adjustable in the stimulation parameters interface 122, but this isn't shown for simplicity.

Stimulation parameters relating to the electrodes 16 are made adjustable in an electrode parameter interface 124. Electrodes are manually selectable in a leads interface 126 that displays a graphical representation of the electrode array 17 or 17' (one or more permanent or trial leads) that has been implanted in a particular patient (a paddle lead 19 is shown as one example). A cursor 128 (or other selection means such as a mouse pointer) can be used to select a particular electrode in the leads interface 126. Buttons in the electrode parameter interface 124 allow the selected electrode (including the case electrode, Ec) to be designated as an anode, a cathode, or off. The electrode parameter interface 124 further allows the amount of the total anodic or cathodic current +I or −I that each selected electrode will receive to be specified in terms of a percentage, X. For example, for the waveforms of FIG. 7, the electrode parameter interface 124 can specify that electrode E1 will receive X=100% of the current I as an anodic current +I (during the first pulse phase 106a) and that electrode E2 will receive X=100% of the current I as a cathodic current −I (again during the first pulse phase 106a). Note that two or more electrodes can be chosen to act as anodes or cathodes at a given time. For example and although not illustrated, suppose E1 will act as an anode, and that electrodes E2 and E3 will act as cathodes at a given time. In this circumstance, the electrode parameter interface 124 can specify that electrode E1 will receive X=100% of the current I as an anodic current +I, that electrode E2 (for example) will receive X=70% of the current I as a cathodic current −0.71, and that electrode E3 will receive the remaining X=30% of the current I as a cathodic current −0.31.

Figure 9:
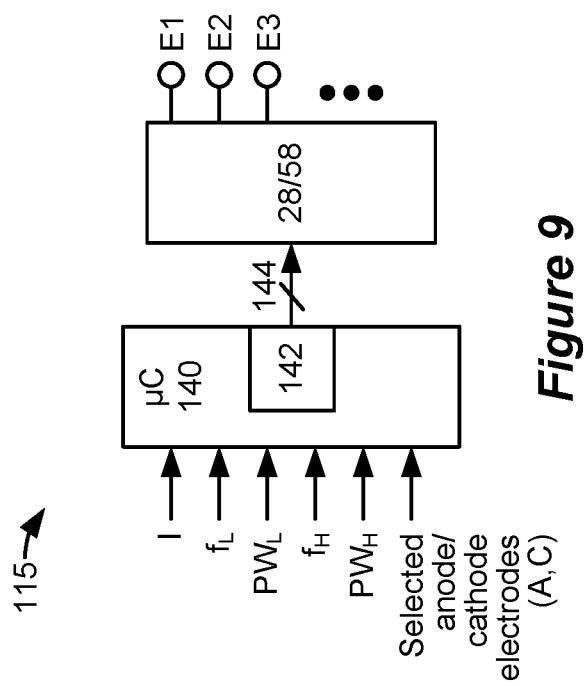
FIG. 9 shows circuitry in the IPG or ETS capable of receiving the stimulation parameters from the GUI and for forming the waveforms of FIG. 7.

FIG. 9 shows an illustration of an IPG or ETS 115 capable of forming the pulses of FIG. 7. As discussed in the Introduction, the stimulation parameters entered from the GUI 120 of FIG. 8 can be wirelessly transmitted by the external device 60 or 70 to an antenna in the IPG or ETS 115, including the amplitude I, low frequency $f_L$, high frequency $f_H$, low-frequency pulse width $PW_L$, high-frequency pulse width $PW_H$, the anode and cathode electrodes (A and C) selected to receive the stimulation pulses, and the relative percentage X of amplitude each anode and cathode is to receive (not shown in FIG. 9 for simplicity).

In FIG. 9, the stimulation parameters, once wirelessly received, are provided to control circuitry 140. Control circuitry 140 may comprise a microcontroller for example, such as Part Number MSP430, manufactured by Texas Instruments, which is described in data sheets at http://www.ti.com/lsds/ti/microcontroller/16-bit_msp430/overview.page? DCMP=MCU_other& HQS=msp430. The control circuitry 140 more generally can comprise a microprocessor, Field Programmable Grid Array, Programmable Logic Device, Digital Signal Processor or like devices. Control circuitry 140 may also be based on well-known ARM microcontroller technology. Control circuitry 140 may include a central processing unit capable of executing instructions, with such instructions stored in volatile or non-volatile memory within or associated with the control circuitry. Control circuitry 140 may also include, operate in conjunction with, or be embedded within an Application Specific Integrated Circuit (ASIC), such as described in U.S. Patent Application Publications 2008/0319497, 2012/0095529, 2018/0071513, or 2018/0071520, which are incorporated herein by reference. The control circuitry 140 may comprise an integrated circuit with a monocrystalline substrate, or may comprise any number of such integrated circuits operating as a system. Control circuitry may also be included as part of a System-on-Chip (SoC) or a System-on-Module (SoM) which may incorporate memory devices and other digital interfaces.

In FIG. 9, the control circuitry 140 includes pulse logic 142, which receives the stimulation parameters and forms various control signals 144 for the stimulation circuitry 28/58. Such control signals 144 specify the timing and polarity of the stimulation pulses appearing at each of the selected electrodes, as well as the amplitude of the current each selected electrode will provide. As relevant to forming the waveforms of FIG. 7, the pulse logic 142 will in particular receive the information relevant to the timing of the waveforms, e.g., $f_L$, $f_H$, $PW_L$, and $PW_H$, and use this information to form the waveforms with the prescribed timing.

Figure 10:
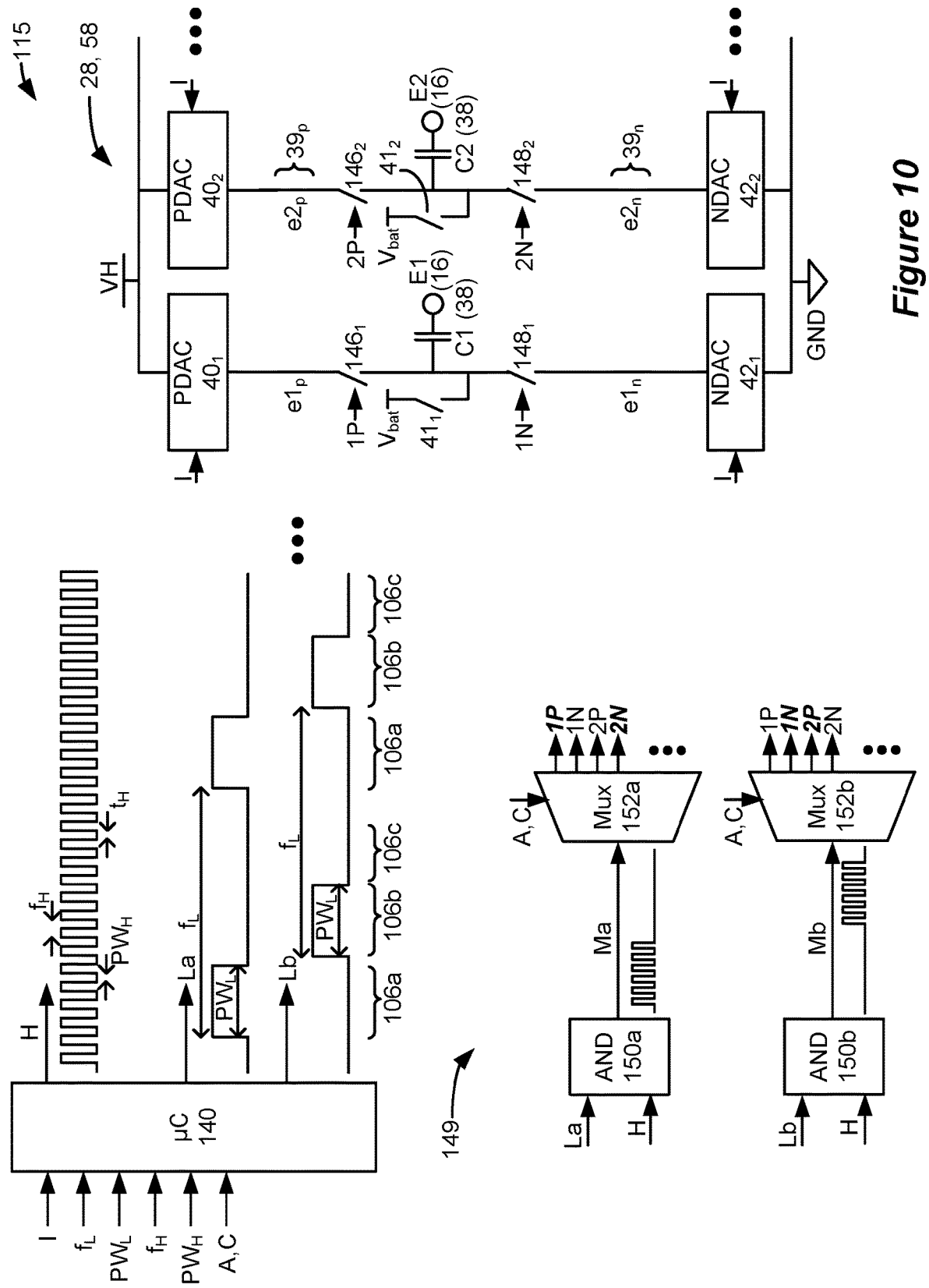
FIG. 10 shows alternative circuitry in the IPG for forming the waveforms of FIG. 7, which circuitry mixes low- and high-frequency digital signals and uses such mixed signals to control the stimulation circuitry in the IPG.

FIG. 10 shows another example of circuitry that can be used to form the pulses of FIG. 7 in IPG or ETS 115. In this example, the control circuitry 140 outputs a high-frequency digital signal H and low-frequency digital signals La and Lb with the appropriate timings and mixes them. The mixed signals are then used to control switches 146i and 148i added to the stimulation circuitry 28/58.

Before describing the digital signals, the stimulation circuitry 28/58 as modified is described. As just mentioned, the stimulation circuitry 28/58 includes a switch 146i in the current path between a given PDAC 40i and a given DC-blocking capacitor Ci, and a switch 148i in the current path between a given NDAC 42i and the DC-blocking capacitor Ci. This establishes different electrode nodes $39_p$ for each PDAC output ($ei_p$) and different electrodes nodes $39_n$ for each NDAC output ($ei_n$). Passive recovery switches 41i are connected between the switches 146i and 148i and as before are coupled to the inside plate of the DC-blocking capacitors 38.

Control circuitry 140 forms a high-frequency digital signal H, which is shown for simplicity as a free running signal. However, this is not strictly necessary, as H may instead only be issued at times that the stimulation circuitry 28/58 is scheduled to issue pulses—i.e., during low-frequency signals La and Lb, as explained further below. High-frequency signal H is formed at high frequency $f_H$ with pulse width $PW_H$, leaving gaps of duration $t_H$ as explained previously.

Control circuitry 140 also forms low-frequency digital signals La and Lb, at a low frequency $f_L$ with pulse width $PW_L$. The timing of La and Lb correspond to the timing of first pulse phase 106a and second pulse phase 106b respectively.

Logic circuitry 149 receives H, La and Lb, and forms control signals for the switches 146i coupled to the PDACs and switches 148i coupled to the NDACs. (Logic circuitry 149 may be implemented and comprise part of control circuitry 140). Specifically, switch 146₁ is controlled by control signal 1P; switch 146₂ is controlled by control signal 2P; etc. Switch 148₁ is controlled by control signal 1N; switch 148₂ is controlled by control signal 2N; etc. Digital signals H and La are mixed to form a digital signal Ma having both the high- and low-frequency timing information, which mixing can be achieved using an AND gate 150a. Likewise, digital signals H and Lb are mixed to form digital signal Mb using AND gate 150b.

Mixed signal Ma is used to control switches 146i and/or 148i during the first pulse phase 106a, while mixed signal Mb is used to control these switches during the second pulse phase 106b. To send Ma and Mb to the correct switches, multiplexers (MUXes) 152a and 152b are used. Both MUXes 152a and 152b are controlled in accordance with the electrodes selected to act as anodes or cathodes during the pulses phases 106a and 106b (A,C).

Thus, to form the pulses of FIG. 7, MUX 152a is informed that electrode E1 will act as an anode during the first pulse phase 106a, and that electrode E2 will act as a cathode during the first pulse phase 106a. This will cause MUX 152a to pass Ma to outputs control signals 1P and 2N, which will open and close switches 146₁ and 148₂ during the first pulse phase 106a and creating the monophasic sub-phase pulses 107a during this period. Note that control circuitry 140 has programmed PDAC 40₁ associated with switch 146₁ and NDAC 42₂ associated with switch 148₂ with the prescribed amplitude I so that the sub-phase pulses 107a will form at electrodes E1 and E2 with the correct amplitude.

Similarly, MUX 152b is informed that electrode E1 will act as a cathode during the second pulse phase 106b, and that electrode E2 will act as an anode during the second pulse phase 106a. This will cause MUX 152b to pass Mb to outputs control signals 1N and 2P, which will open and close switches 146₂ and 148₁ during the second pulse phase 106b, thus creating the monophasic sub-phase pulses 107b during this period. Again, control circuitry 140 has programmed PDAC 40₂ associated with switch 146₂ and NDAC 42₁ associated with switch 148₁ with the prescribed amplitude I.

FIGS. 11A-11C show other examples of stimulation waveforms having both low frequency ($f_L$) and high frequency ($f_H$) features. For simplicity, the waveform at only a single selected electrode (e.g., E1) is shown, although it should be understood that one or more electrodes (e.g., E2) would also be active and of the opposite polarity to ensure that the net current injected into the tissue at any time is zero, as occurred in FIG. 7.

The waveforms of FIGS. 11A and 11B are similar to those of FIG. 7 in that each pulse is issued at a low frequency $f_L$ and comprises a first phase 160a followed by a second phase 160b. Each pulse phase 160a and 160b is also fractionalized into monophasic sub-phase pulses 161a and 161b issued at a high frequency $f_H$, which sub-phase pulses are separated by gaps 162. Although not shown, the same durations described earlier with reference to FIG. 7 ($PW_L$, $PW_H$, $t_H$, etc.) can apply to the phases and sub-phases shown in FIG. 11.

In FIG. 11A, the current amplitudes of the sub-phase pulses 161a and 161b are not constant over the duration of the first and second pulse phases 160a and 160b, but instead vary. The variation in the amplitudes is similar during phases 160a and 160b (with each ramping up and the down), but this isn't required. For example, the amplitudes of sub-phase pulses 161a during the first pulse phase 160a could vary, while the amplitudes of sub-phase pulses 161b during the second pulse phase 160b could vary differently or be constant. Nonetheless, the two phases 160a and 160b are charge balanced at each electrode, i.e., with the total charge provided by the sub-phase pulses 161a equaling +Q during the first pulse phase 160a and the total charge provided by the sub-phase pulses 161b equaling −Q during the second pulse phase 160b.

In FIG. 11B, the current amplitudes of the sub-pulses 161a and 161b are constant over the duration of the first and second pulse phases 160a and 160b, but the high-frequency pulse widths $PW_H$ of the sub-phase pulses 161a and 161b vary during each of the pulse phases. The variation in the pulse width $PW_H$ is similar during phases 160a and 160b, but again this isn't required. For example, the pulse width $PW_H$ of sub-phase pulses 161a during the first pulse phase 160a could vary, while the pulse width $PW_H$ of sub-phase pulses 161b during the second pulse phase 160b could vary differently or be constant. Nonetheless, the two phases 160a and 160b are charge balanced at each electrode, i.e., with the charge provided by the sub-phase pulses 161a equaling +Q during the first pulse phase 160a and the charge provided by the sub-phase pulses 161b equaling −Q during the second pulse phase 160b. Note also that the high frequency of the sub-phase pulses 161a and 161b may vary within each of the pulse phases 160a and 160b.

In FIG. 11C, charge balancing at each electrode is provided even though sub-phase pulses are provided during only one of the pulse phases 160a or 160b. For example, in FIG. 11C, only first pulse phase 160a has monophasic sub-phase pulses 161a (of total charge +Q); the second pulse phase 160b comprises a constant pulse 110a or 110b (of charge −Q). The duration or amplitude of the constant pulse 110a or 110b can vary. For example, constant pulse 110a has a pulse width equal to the duration of the first pulse phase 160a, but an amplitude −I' that is smaller than the amplitude +I of the sub-phase pulses 161a. Constant pulse 110b has an amplitude −I equal to the amplitude +I of the sub-phase pulses 161a, but has a pulse width that is smaller than the duration of the first pulse phase 160a. In either case, the charged is balanced during both pulses phases 160a and 160b (+Q=|−Q|).

Figure 12A:
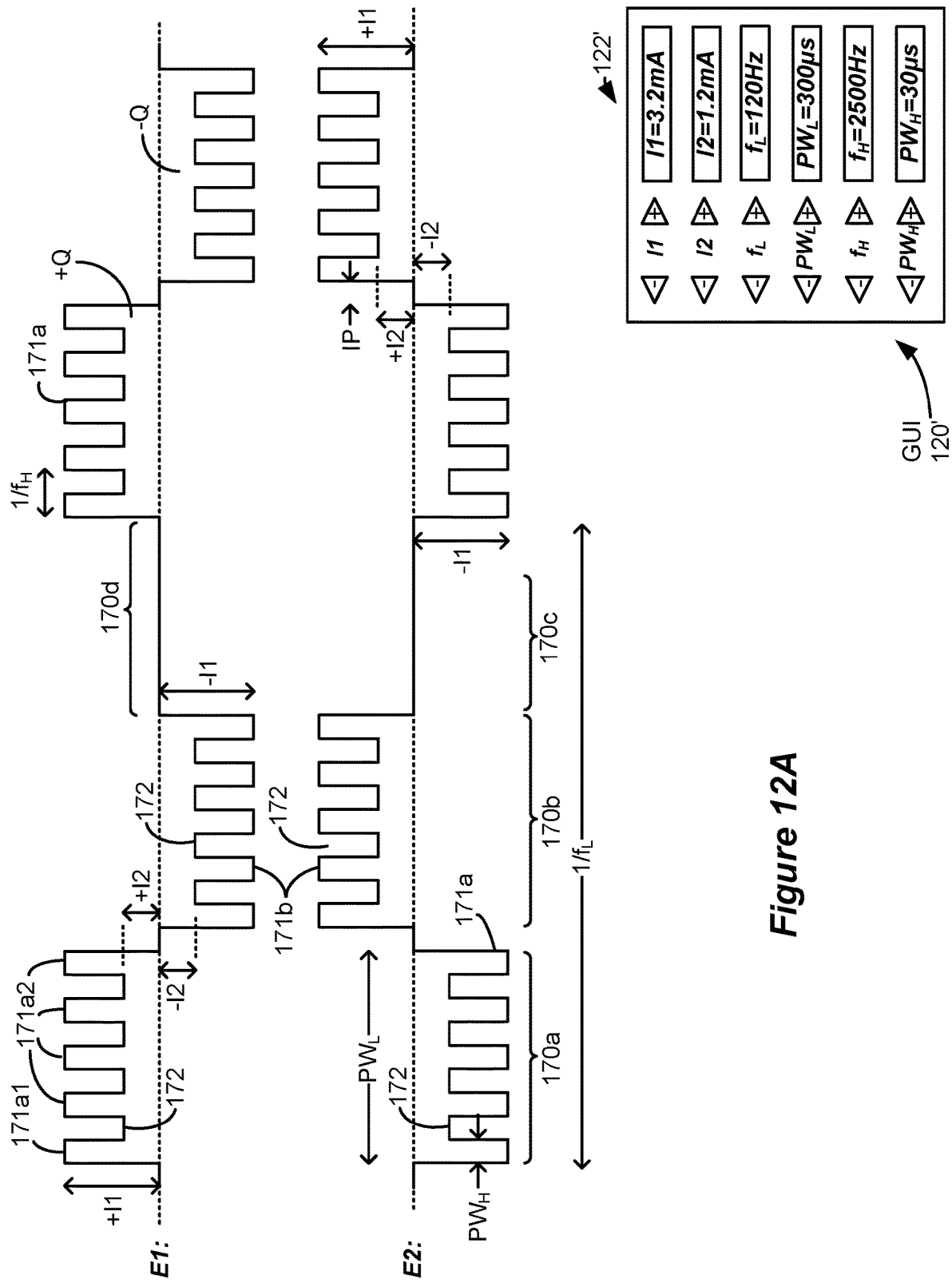
FIGS. 12A and 12B show second examples of waveforms producible by the IPG or ETS at electrodes and having both low- and high-frequency aspects in accordance with the invention, having charge-balanced first and second pulse phases, in which each pulse phase is comprised of high-frequency monophasic sub-pulses which do not return to zero during the gaps between the sub-pulses.

FIG. 12A shows another example of stimulation waveforms having both low frequency ($f_L$) and high frequency ($f_H$) features. Different in the waveforms of FIG. 12A are current levels provided during the gaps 172 between the sub-phase pulses 171a and 171b. In FIG. 7, the current returned to zero during the gaps 108 between the sub-phase pulses 107a and 107b. In FIG. 12A however, the current does not return to zero during the gaps 172, but instead returns to a smaller magnitude current of the same polarity as the sub-phase pulses 171a and 171b. Thus, during first phase 170a, electrode E1's sub-phase pulses 171a are positive, and have a magnitude of +I1. During the gaps 172, the current returns to a smaller positive value of +I2. Electrode E2's waveform during the first phase 170a is similar, but of opposite polarity to ensure that a net amount of current is not delivered to the patient's tissue. E2's sub-phase pulses 171a are thus negative with a magnitude of −I1, with the current returning to a smaller negative value of −I2. During the second pulse phase 170b, electrode E1's sub-phase pulses 171b are negative with a magnitude of −I1, and returning to −I2 during the gaps 172; electrode E2's sub-phase pulses 171b are positive with a magnitude of +I1, and returning to +I2 during the gaps 172. A passive recovery period 170c can occur during quiet periods between the pulses as before.

Preferably the waveforms of FIG. 12A are formed in a single timing channel as discussed earlier.

The waveforms of FIG. 12A can be beneficial, because a small non-zero return current (I2) during gaps 172 can enhance polarization of neural fibers. The combination of the polarizing return current (I2) with superimposed higher-intensity sub-phase pulses 171a and 171b (I1) can create changes in excitability and recruitment order. For example, large fibers can be excited once, such as during a first sub-phase pulse 171a1 in first pulse phase 170a, while smaller fibers are excited multiple times by all of the sub-phase pulses 171a in the first pulse phase 170a, or at least during subsequent sub-phase pulses 171a2.

FIG. 12A also shows how the GUI 120 (FIG. 8) can be modified to form the waveforms of FIG. 12A. Specifically, the stimulation parameters interface 122' of GUI 120' has been changed to add for the setting or adjustment of the two current levels I1 and I2 used to define the pulses. Settings to adjust the low ($f_L$) and high ($f_H$) frequency aspects of the pulses, and pulse widths $PW_L$ and $PW_H$, can be included as before, as can other aspects not shown in FIG. 12A.

Figure 12B:
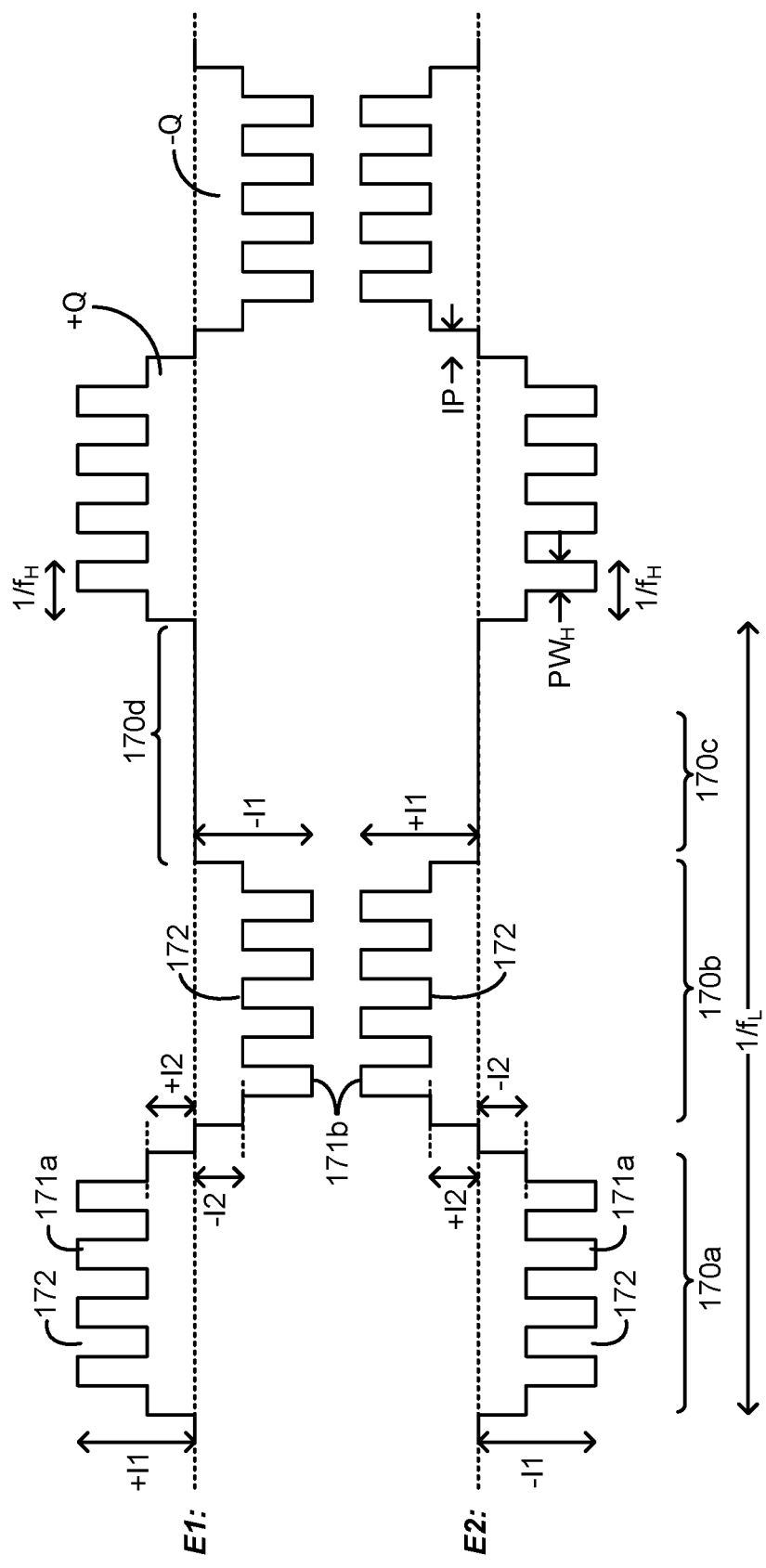

FIG. 12B shows a modification to the waveforms of FIG. 12A. In this example, the non-zero return current (I2) is established at the beginning and end of each of the pulses phases 170a and 170b. That is, the pulse phases 170a and 170b start and end with the non-zero return current, rather than starting and ending with the sub-phase pulses 171a and 171b (I1), as occurred in FIG. 12A. Particularly at the start of the phases 170a and 170b, providing the non-zero return current before the sub-phase pulses can assist in neural polarization, and hence selective recruitment of different neural fibers as described earlier.

FIGS. 13A-13F show other examples of stimulation waveforms having both low frequency ($f_L$) and high frequency ($f_H$) features, and similar to FIGS. 12A and 12B in that the current does not return to zero in gaps 182 between the sub-phase pulses 181a and 181b. Again, the waveform at only a single selected electrode (e.g., E1) is shown.

In FIG. 13A, the current amplitudes of the sub-phase pulses 181a and 181b, the non-zero return current during gaps 182, or both, are not constant over the duration of the first and second pulse phases 180a and 180b, but instead vary. Thus, during the first pulse phase 180a, the amplitude of the sub-phase pulses 181a varies as value +I1, while the amplitude of return current varies as value +I2, both shown generally with dotted lines. During the second pulse phase 180b, the amplitude of the sub-phase pulses 181b and the non-zero return current vary as values −I1 and −I2. Nonetheless, the two phases 180a and 180b are preferably charge balanced at each electrode, i.e., with the charge provided by the sub-phase pulses 181a and the non-zero return current equaling +Q during the first pulse phase 180a and the charge provided by the sub-phase pulses 181b and the non-zero return current equaling −Q during the second pulse phase 180b.

FIG. 13B shows another example in which only the amplitude of the non-zero return current (I2) during gaps 182 varies, and specifically is ramped; the amplitude of the sub-phase pulses 181a and 181b are held constant (I1). The variation in the amplitudes in FIGS. 13A and 13B are shown to vary similarly during phases 180a and 180b, but as before this isn't required. For example, in FIG. 13C, the amplitude of the non-zero return current and the sub-phase pulses 181a are constant during the first pulse phase 180a; however, the amplitude of the non-zero return current varies during the second pulse phases 180b. The amplitude of the sub-phase pulses 181b could also vary during the second pulse phase 180b, although this isn't shown in FIG. 13C. Even if the pulse phases 180a and 180b are not symmetrical as shown in FIG. 13C, they can still be charge balanced (+Q and –Q).

In FIG. 13D, the current amplitudes of the sub-pulses 181a and 181b (+I1 or –I1) and the return currents (+I2 and –I2) are constant over the duration of the first and second pulse phases 180a and 180b, but the high-frequency pulse widths PW$_H$ of the sub-phase pulses 181a and 181b vary during each of the pulse phases. The variation in the pulse width PW$_H$ is again shown to vary similarly during phases 180a and 180b, but this isn't required. Again, the two phases 180a and 180b are charge balanced at each electrode (+Q=|–Q|).

In FIG. 13E, charge balancing at each electrode is provided even though sub-phase pulses are provided during only one of the pulse phases 180a or 180b. For example, in FIG. 13E, only first pulse phase 180a has monophasic sub-phase pulses 181a and a non-zero return current (of total charge +Q); the second pulse phase 180b comprises a constant pulse 112a or 112b (of charge –Q). The duration or amplitude of the constant pulse 112a or 112b can vary. For example, constant pulse 112a has a pulse width equal to the duration of the first pulse phase 180a, but an amplitude –I3 that is smaller than the amplitude +I1 of the sub-phase pulses 181a and larger than the amplitude +I2 of the non-zero return current. Constant pulse 112b has an amplitude –I1 equal to the amplitude +I1 of the sub-phase pulses 181a, but has a pulse width that is smaller than the duration of the first pulse phase 180a. In either case, the charged is balanced during both pulses phases 180a and 180b (+Q=|–Q|).

FIG. 13F shows a different example of waveforms in which the non-zero return current is equal and of the same polarity in both of the pulse phases 180a and 180b. In the first pulse phase 180a, sub-phase pulses 181a are provided having a positive amplitude of +I1. However, in the gaps 182 between the sub-phase pulses 181a, the non-zero return current is negative, having an amplitude of –I2. In total, the first pulse phase 180a can have a net charge of +Q, with the positive sub-phase pulses 181a adding to this net value and the negative return current subtracting from this net value. In the second pulse phase 180b, the sub-phase pulses 181b have a negative amplitude of –I3. In the gaps 182 between the sub-phase pulses 181b, the non-zero return current has the same negative amplitude of –I2 that occurred in the first pulse phases 180a. In total, the second pulse phase 180b can have a net charge of –Q, with the negative sub-phase pulses 181b and the negative return current contributing to this net charge. To achieve charge balance between the first and second pulses phases 180a and 180b (+Q and –Q), the absolute value of –I3 would be smaller than +I1. The waveform of FIG. 13F can be beneficial because it provides the same degree of neural polarization during the gaps 182 in both of the pulse phases 180a and 180b.

Figures 14A, 14B, 14C:
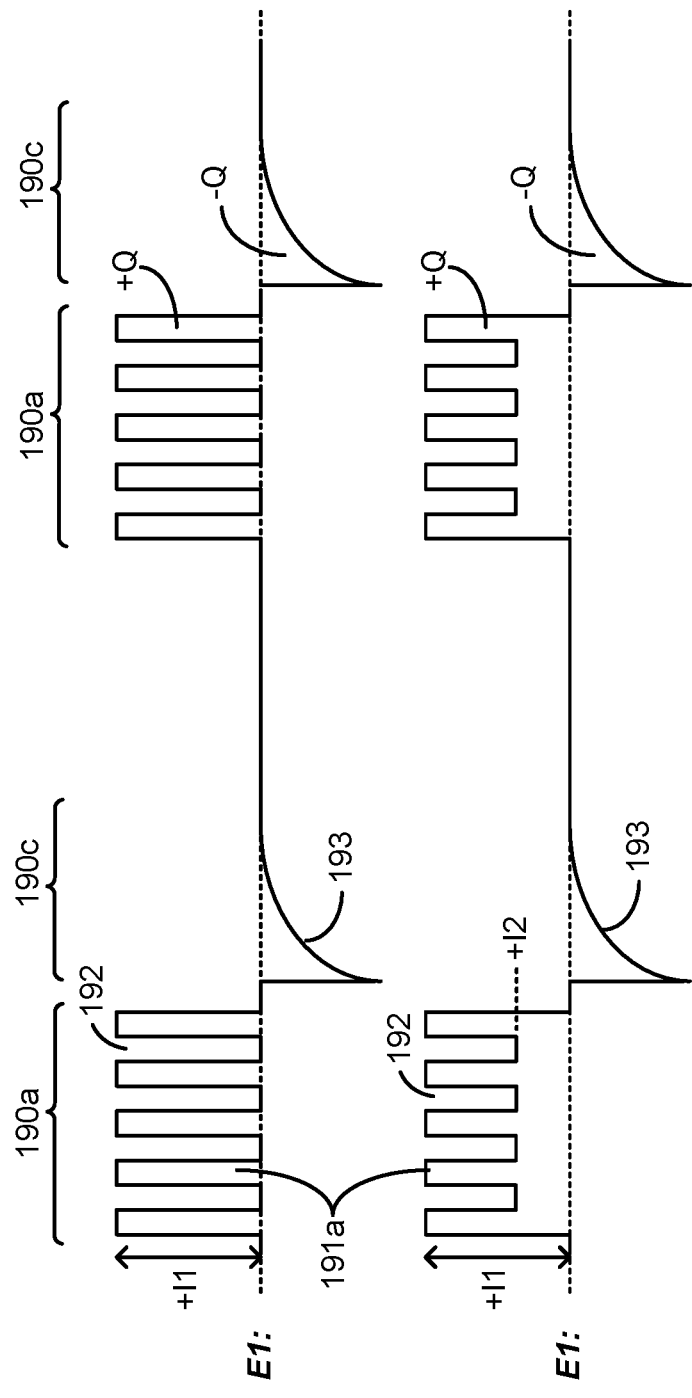
FIGS. 14A and 14B show examples of waveforms in which active first pulses phases are followed by passive recovery phases.
FIG. 14C shows passive recovery circuitry.

The waveforms illustrated can also be used with passive charge recovery. This is shown in FIGS. 14A and 14B for a waveform having a zero return current during gaps 192 (FIG. 14A), and a waveform having a non-zero return current during gaps 192 (FIG. 14B). In these examples, sub-phase pulses 191a and the non-zero return current (FIG. 14B only) are actively driven by the stimulation circuitry 28 (FIG. 3) only during a first pulse phase 190a. There is no actively-driven second pulse phase. Instead, a passive recovery phase 190c is provided after the first pulse phase 190a. As explained earlier, passive recovery can recover charge stored on capacitive elements in the current path (e.g., between electrodes E1 and E2), such as the DC-blocking capacitors 38. This occurs using passive recovery switches 41$_i$, as shown in the circuit diagram of FIG. 14C. After the first pulse phase 190a, capacitors C1 and C2 38 coupled to the electrodes E1 and E2 would be charged (Vc1, Vc2) with the polarities as shown. When the passive recovery switches 41$_1$ and 41$_2$ connected to electrode nodes e1 and e2 39 are closed during the passive recovery phase 190c, the electrode nodes are shorted to a reference voltage (e.g., Vbat). This causes the charge on the capacitors to equilibrate, causing a current 193 flow from E2 to E1 through the patient's tissue, R. Given the R-C nature of this circuit, this current 193 will exponentially decay, and assuming the passive recovery switches 41$i$ are closed for a long enough duration, the voltages across the capacitors and the resulting current 193 will decay to zero. Thus, the charge of the first pulse phases (+Q) is passively recovered during the passive recovery phase 190c (–Q).

To this point, the waveforms have been shown as having pulses with only two phases, such as the first and second pulse phases 106a and 106b of FIG. 7, the first and second pulse phases 170a and 170b of FIG. 12A, or the first and passive recovery pulse phases 190a and 190b of FIGS. 14A and 14B. However, each pulse could have more than two pulse phases, and all pulse phases can be charged balanced with a pulse, although this is not illustrated for simplicity.

The modifications to the various waveforms illustrated to this point can be combined in different manners, even if such combinations are not illustrated in the figures. It is not practical to illustrate all of these possible combinations, but it should be understood that any combination of the various modifications can be used in a practical implementation and are within the scope of this disclosure.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A stimulator device, comprising:
 a plurality of electrode nodes, each electrode node configured to be coupled to one of a plurality of electrodes configured to contact a patient's tissue; and
 stimulation circuitry configured to provide a sequence of pulses at at least two of the electrode nodes selected to create a stimulation current through the patient's tissue,
 wherein the stimulation circuitry is configured to receive a first amplitude and a second amplitude lower than the first amplitude, and to form each pulse at the selected electrode nodes with a first phase and a second phase,
 wherein one of the first or second phases at each selected electrode node comprises a plurality of monophasic sub-phase pulses of a first polarity and of the first amplitude, wherein the monophasic sub-phase pulses are separated by first gaps, wherein a non-zero current of the first polarity and of the second amplitude is provided during the first gaps,
 wherein at each selected electrode node a first total charge of the plurality of monophasic sub-phase pulses plus the non-zero current is equal but opposite a second total charge of the second phase.

2. The stimulator device of claim 1, further comprising a case for housing the stimulation circuitry, wherein the case is conductive, and wherein the conductive case comprises one of the plurality of electrodes.

3. The stimulator device of claim 1, wherein at least one selected electrode node is coupled to its associated electrode through a DC-blocking capacitor.

4. The stimulator device of claim 1, further comprising at least one implantable lead, wherein the electrodes are located on the lead.

5. The stimulator device of claim 1, wherein the first amplitude comprises a constant current amplitude.

6. The stimulator device of claim 5, wherein the second amplitude comprises a constant current amplitude.

7. The stimulator device of claim 1, wherein the other of the first or second phases at each selected electrode node comprises a plurality of monophasic sub-phase pulses of a second polarity opposite the first polarity and of the first amplitude, wherein the monophasic sub-phase pulses are and separated by second gaps, wherein a non-zero current of the second polarity and of the second amplitude is provided during the second gaps.

8. The stimulator device of claim 1, wherein the other of the first or second phases at each selected electrode node comprises a constant pulse.

9. The stimulator device of claim 1, wherein a pulse width of the monophasic sub-phase pulses varies during the one of the first or second phases.

10. The stimulator device of claim 1, wherein a frequency of the monophasic sub-phase pulses varies during the one of the first or second phases.

11. The stimulator device of claim 1, further comprising control circuitry, wherein the control circuitry is configured to receive stimulation parameters including a first frequency of the pulses, a second frequency of the monophasic sub-phase pulses, a pulse width of at least one of the first and second phases, and a pulse width of the monophasic pulses, wherein the control circuitry is configured to use the stimulation parameters to provide a plurality of control signals to the stimulation circuitry inclusive of the first amplitude and the second amplitude to cause the stimulation circuitry to form the sequence of pulses at the selected electrode nodes.

12. The stimulator device of claim 11, further comprising an antenna, wherein the control circuitry is configured to receive the stimulation parameters from the antenna.

13. The stimulator device of claim 1, wherein the stimulator device comprises an implantable pulse generator.

14. The stimulator device of claim 1, wherein the stimulator device comprises an external stimulator.

15. The stimulator device of claim 1, wherein the stimulation circuitry is configured to form an interphase period at the selected electrode nodes between the first phase and the second phase, wherein no current is issued to the tissue during the interphase period.

16. The stimulator device of claim 1, wherein the monophasic sub-phase pulses are positive at at least one of the selected electrode nodes and negative at at least one other of the selected electrode nodes such that the net current injected into the tissue at any time is zero during the one of the first or second phases.

17. The stimulator device of claim 1, wherein the stimulation circuitry is configured to provide the sequence of pulses in a single timing channel.

* * * * *